United States Patent [19]
Hall et al.
[11] Patent Number: 4,734,424
[45] Date of Patent: Mar. 29, 1988

[54] BICYCLOHEPTANE SUBSTITUTED DIAMIDE AND ITS CONGENER PROSTAGLANDIN ANALOGS

[75] Inventors: Steven E. Hall, Ewing Township, Mercer County; Joyce Reid, Dayton, both of N.J.

[73] Assignee: E. R. Squibb & Sons, Inc., Princeton, N.J.

[21] Appl. No.: 911,173

[22] Filed: Sep. 24, 1986

[51] Int. Cl.$^4$ .................... C07C 177/00; A61K 31/557

[52] U.S. Cl. .................................... 514/382; 514/530; 514/573; 514/616; 548/253; 560/27; 560/41; 560/120; 562/450; 562/502; 564/152; 564/153; 564/155

[58] Field of Search ............................ 560/120, 27, 41; 562/502, 450; 564/152, 153, 155; 548/253; 514/382, 530, 573, 616

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,436,934 | 3/1984 | Larock | 562/502 |
| 4,456,615 | 6/1984 | Nakane et al. | 424/285 |
| 4,456,617 | 6/1984 | Nakane et al. | 424/285 |
| 4,542,160 | 9/1985 | Sprague et al. | 514/569 |
| 4,638,012 | 1/1987 | Nakane | 514/469 |
| 4,647,585 | 3/1987 | Loots | 514/530 |

FOREIGN PATENT DOCUMENTS

| | | |
|---|---|---|
| 0043292 | 8/1982 | European Pat. Off. . |
| 0082646 | 6/1983 | European Pat. Off. . |
| 2039909 | 8/1980 | United Kingdom . |

*Primary Examiner*—Robert Gerstl
*Attorney, Agent, or Firm*—Lawrence S. Levinson; Burton Rodney

[57] ABSTRACT

Bicycloheptane substituted amide prostaglandin analogs are provided having the structural formula

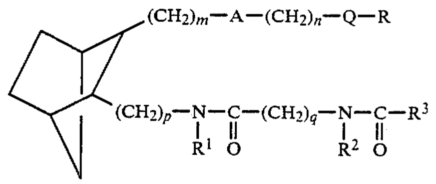

wherein m is 0 to 4; A is —CH=CH— or —CH$_2$—CH$_2$—; n is 1 to 5; Q is —CH=CH—, —CH$_2$—,

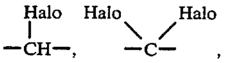

or a single bond; R is $CO_2H$, $CO_2$alkyl, $CO_2$alkali metal, $CO_2$polyhydroxyamine salt, —$CH_2OH$,

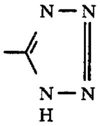

, or

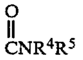

wherein $R^4$ and $R^5$ are the same or different and are H, lower alkyl, hydroxy, lower alkoxy or aryl, at least one of $R^4$ and $R^5$ being other than hydroxy and lower alkoxy; p is 1 to 4; $R^1$ is H or lower alkyl; q is 1 to 12; $R^2$ is H or lower alkyl; and $R^3$ is H, lower alkyl, lower alkenyl, lower alkynyl, aryl, arylalkyl, lower alkoxy, aryloxy, arylalkyloxy, amino, alkylamino arylamino, arylalkylamino, lower alkyl-S-, aryl-S-, arylalkyl-S-,

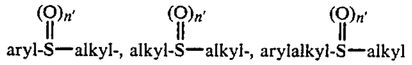

(wherein n' is 0, 1 or 2), alkylaminoalkyl, arylaminoalkyl, arylalkylaminoalkyl, alkoxyalkyl, aryloxyalkyl or arylalkoxyalkyl.

The compounds are cardiovascular agents useful, for example, in the treatment of thrombotic disease.

14 Claims, No Drawings

BICYCLOHEPTANE SUBSTITUTED DIAMIDE AND ITS CONGENER PROSTAGLANDIN ANALOGS

DESCRIPTION OF THE INVENTION

The present invention relates to cycloheptane substituted diamides and congener prostaglandin analogs which are cardiovascular agents useful, for example, in the treatment of thrombotic disease. These compounds have the structural formula

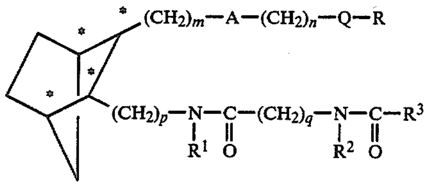

I including all stereoisomers thereof, wherein m is 0 to 4; A is —CH=CH— or —$CH_2$—$CH_2$—; n is 1 to 5; Q is —CH=CH—, —$CH_2$,

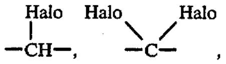

or a single bond; R is $CO_2H$, $CO_2$alkyl, $CO_2$ alkali metal, $CO_2$polyhydroxyamine salt,

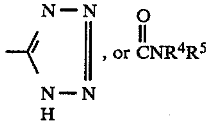

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; $R^2$ is H or lower alkyl; and $R^3$ is H, lower alkyl, lower alkenyl, lower alkynyl, aryl, arylalkyl, lower alkoxy, arylalkyloxy, aryloxy, amino, alkylamino, arylalkylamino, arylamino, lower alkyl-S-, aryl-S-, arylakyl-S-,

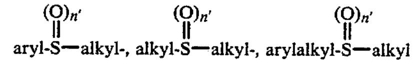

(wherein n' is 0, 1 or 2), alkylaminoalkyl, arylaminoalkyl, arylalkylaminoalkyl, alkoxyalkyl, aryloxyalkyl or arylalkoxyalkyl.

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkylaryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The terms $(CH_2)_m$, $(CH_2)_n$ and $(CH_2)_p$ includes straight or branched chain radicals having from 0 to 4 carbons in the normal chain in the case of $(CH_2)_m$, from 1 to 5 carbons in the normal chain in the case of $(CH_2)_n$ and from 1 to 4 carbons in the normal chain in the case of $(CH_2)_p$ and may contain one or more lower alkyl and/or halogen substituents. Examples of $(CH_2)_m$, $(CH_2)_n$ and $(CH_2)_p$ groups include

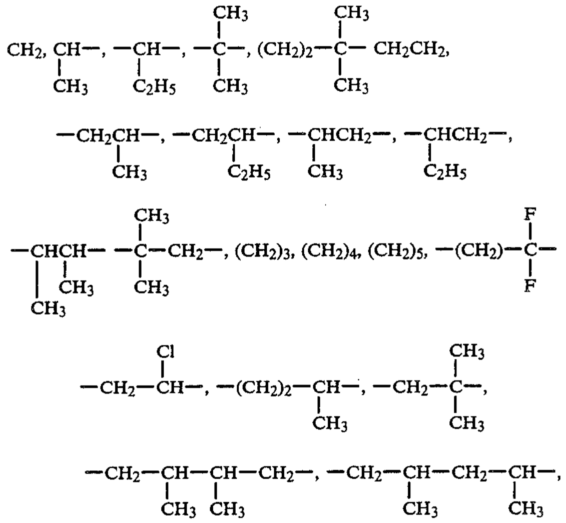

and the like.

The term $(CH_2)_q$ includes straight or branched chain radicals having from 1 to 12 carbons in the normal chain and includes any of the above examples of $(CH_2)_m$, $CH_2)_n$ and $(CH_2)_p$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

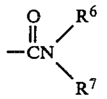

wherein $R^6$ and $R^7$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein m is 1 or 2, A is a —CH=CH—, n is 1 or 4, Q is a single bond or $—C(F_2)—$, $(CH_2)_2$, or —CH=CH—, R is $CO_2H$ or $CH_2OH$; p is 1, $R^1$ is H, $(CH_2)_q$ is $—CH_2—$; $R^2$ is H or $CH_3$, and $R^3$ is lower alkyl, such as pentyl, hexyl, or heptyl or lower alkoxy, such as pentoxy, lower alkylamino such as pentylamino or arylthioalkyl, such as phenylthiomethyl.

The compounds of formula I of the invention may be prepared as described below.

A. p is 1, m is 1, Q is $—CH_2—$ or a single bond and $R^1$ is H

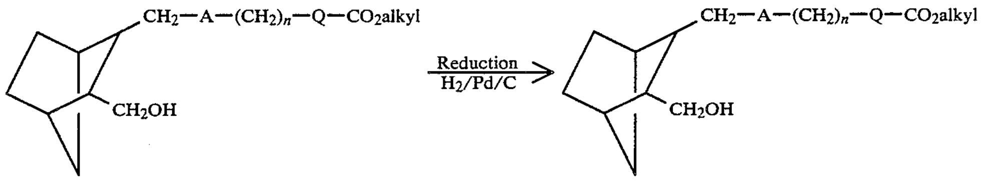

II
(where A is —CH=CH—)

IIA
(where A is $—(CH_2)_2—$)

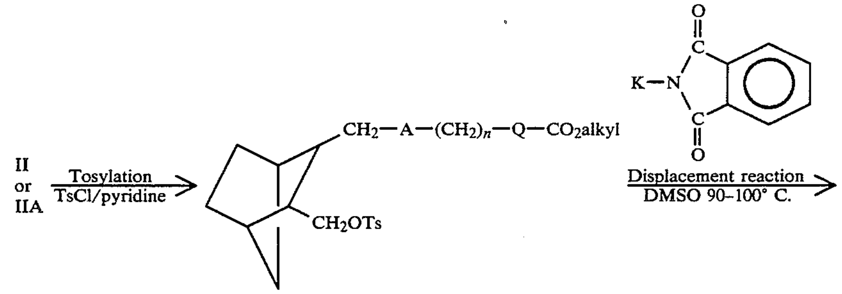

IV

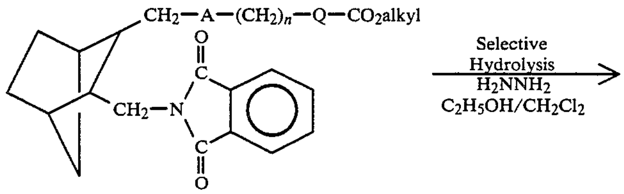

V

-continued
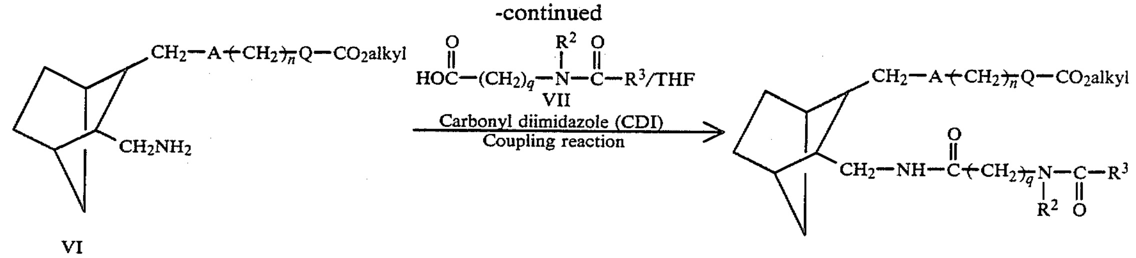
VI IA
A'. Where p is 1, m is 1, Q is $-CH_2-$ or a single bond and $R^1$ is alkyl
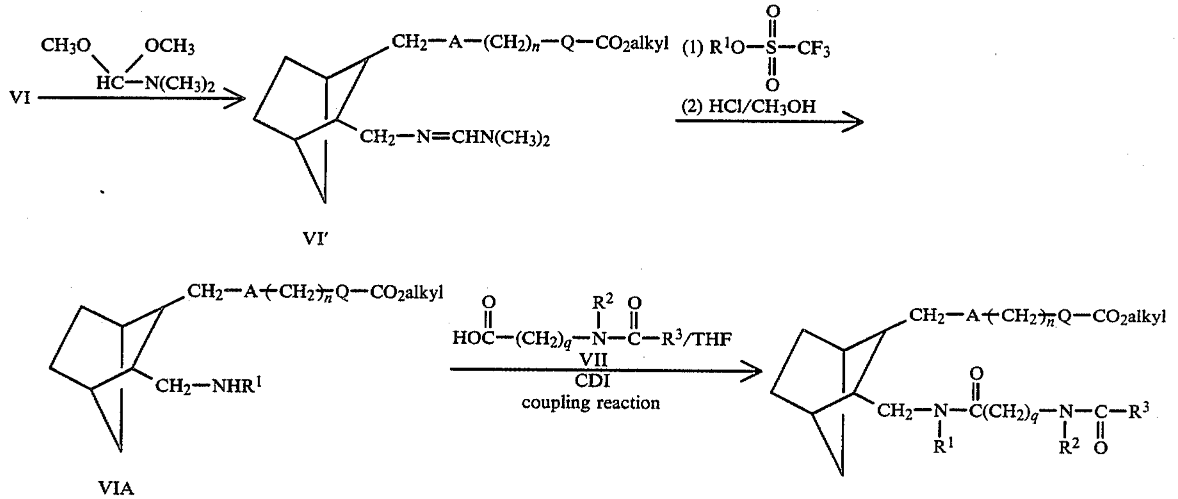
VI' VIA IA'
B. Where Q is $CH_2$ or a single bond, p is 2 to 5, m is 1 and $R^1$ is H
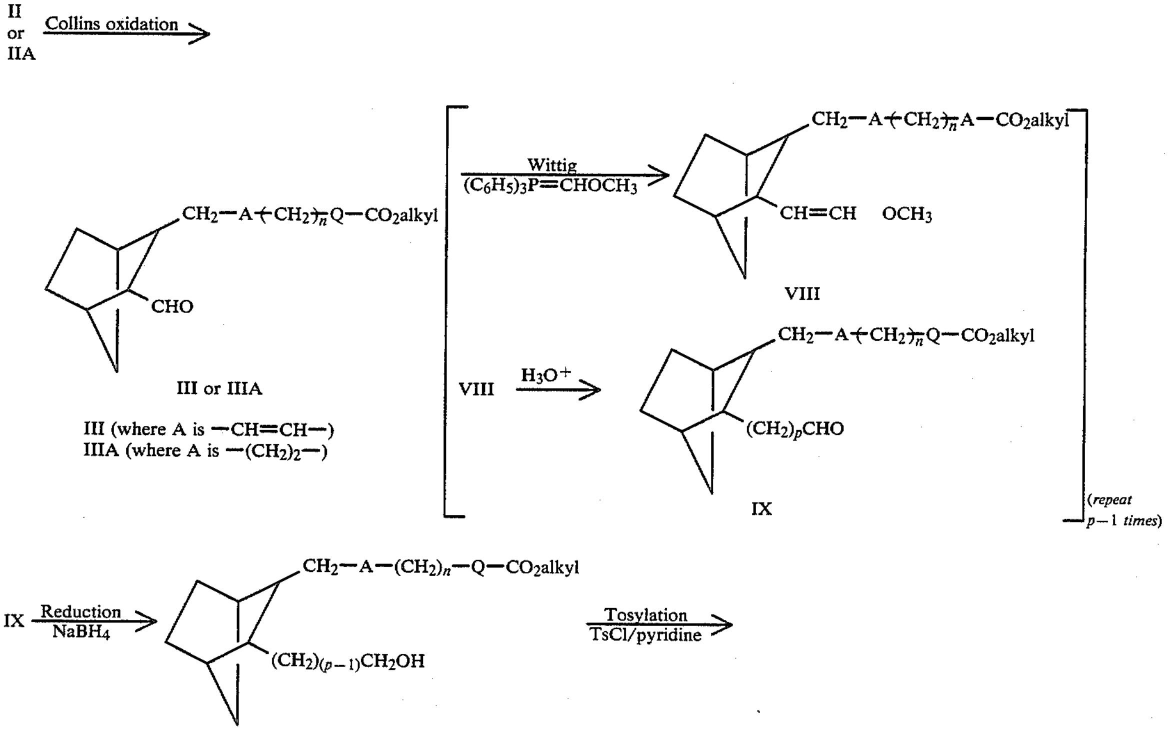
III or IIIA
III (where A is $-CH=CH-$)
IIIA (where A is $-(CH_2)_2-$)
VIII IX IXA -continued
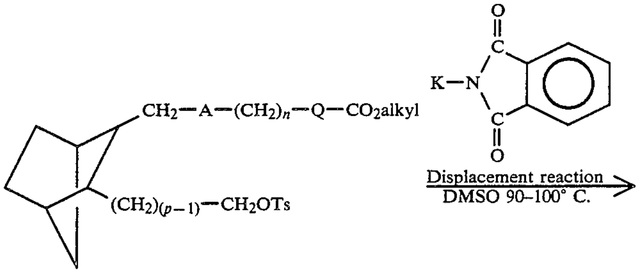
X
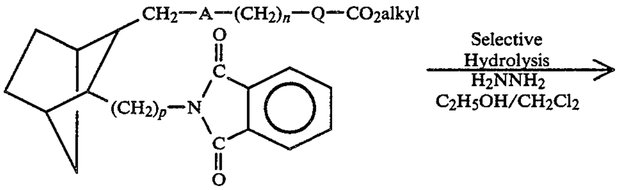
XI
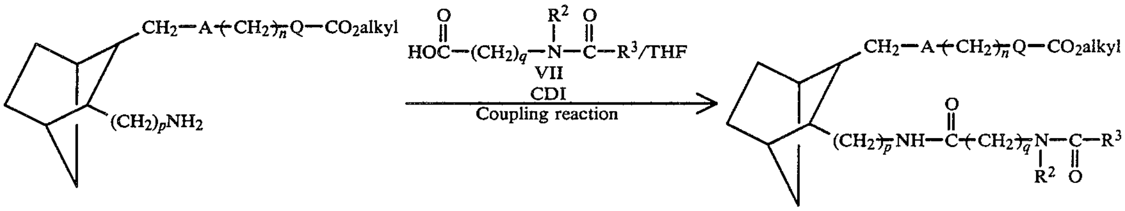
XII
IB
B'. Where Q is $CH_2$ or a single bond, p is 2 to 5, m is 1 and $R^1$ is alkyl
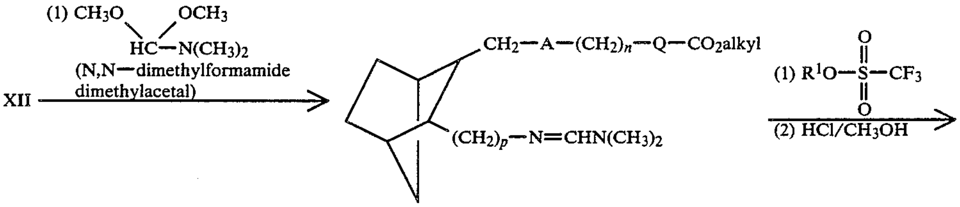
XII'
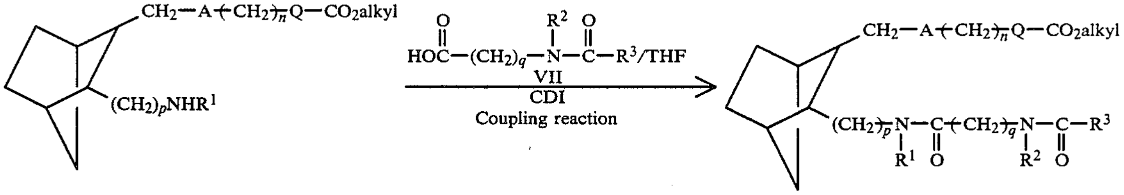
XIIA
IB'
C. Where m is 2, p is 1, A is —CH=CH— and Q is $CH_2$ or a single bond
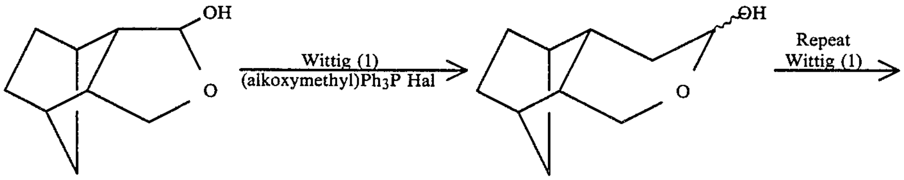
XIII
F -continued
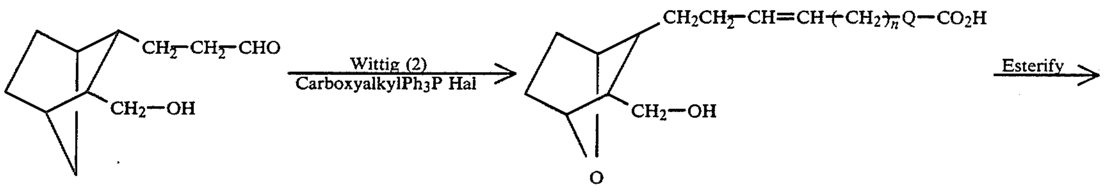
XIV XV
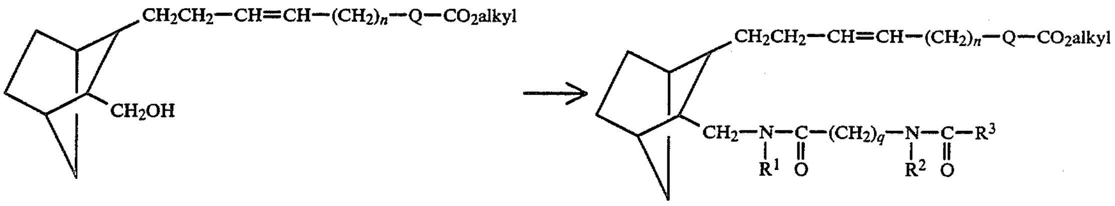
XVI IC
D. m is 2, p is 1, A is $-CH_2-CH_2-$ and Q is $CH_2$ or a single bond
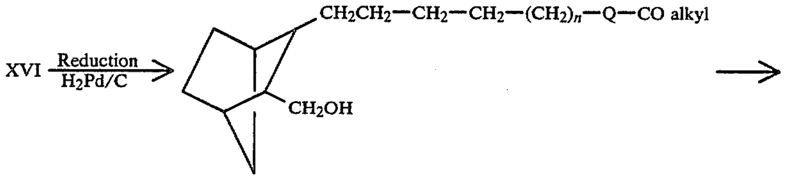
XVIA
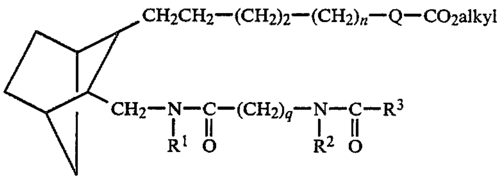
ID
E. Where m is 3 or 4, p is 1, A is $-CH=CH-$ and Q is $CH_2$ or a single bond
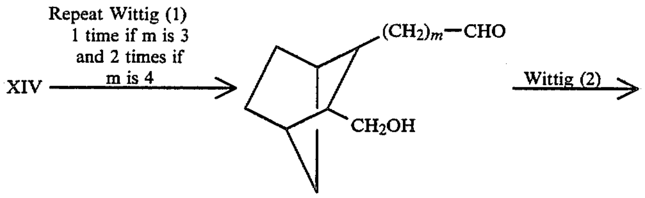
XVII
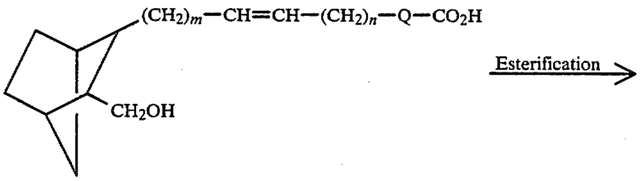
XVIII -continued
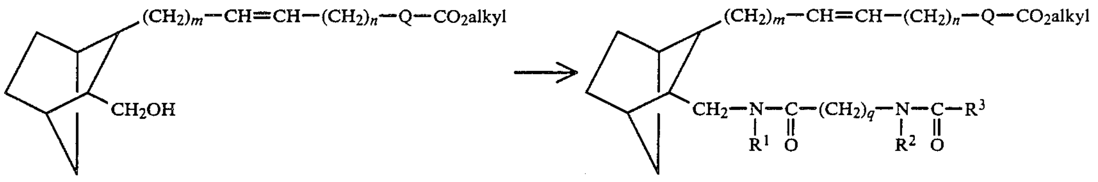
XIX IE
F. Where m is 3 or 4, p is 1, A is $CH_2CH_2$ and Q is $CH_2$ or a single bond
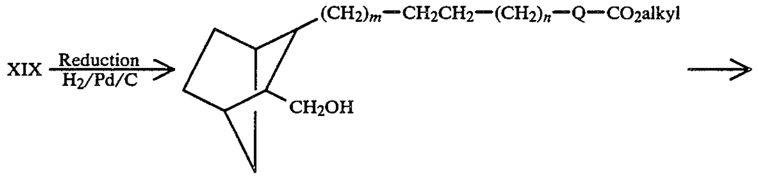
XIXA
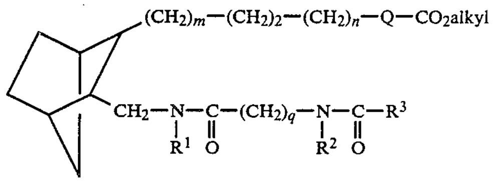
IF
G. Where m = 0, A is $-CH{=}CH-$, p is 1, Q is $CH_2$ or a single bond
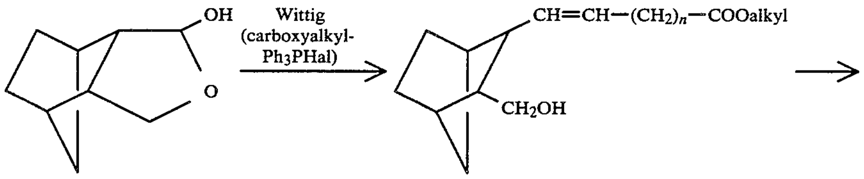
XIII IXB
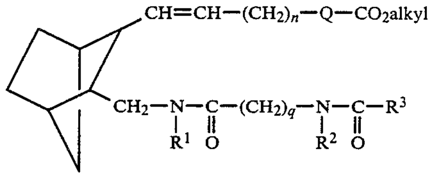
IG
H. Where m = 0, A is $-(CH_2)_2-$, p is 1, Q is $CH_2$ or a single bond
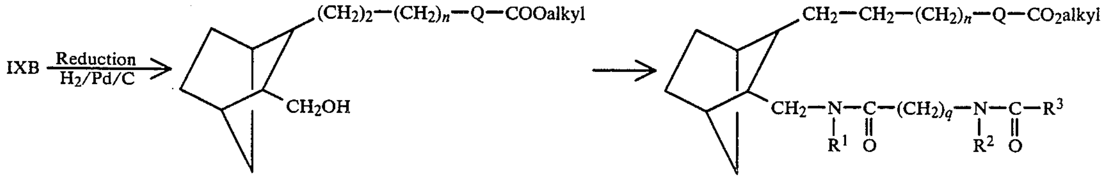
IXC IH
I. Where Q is $-CH{=}CH-$ -continued
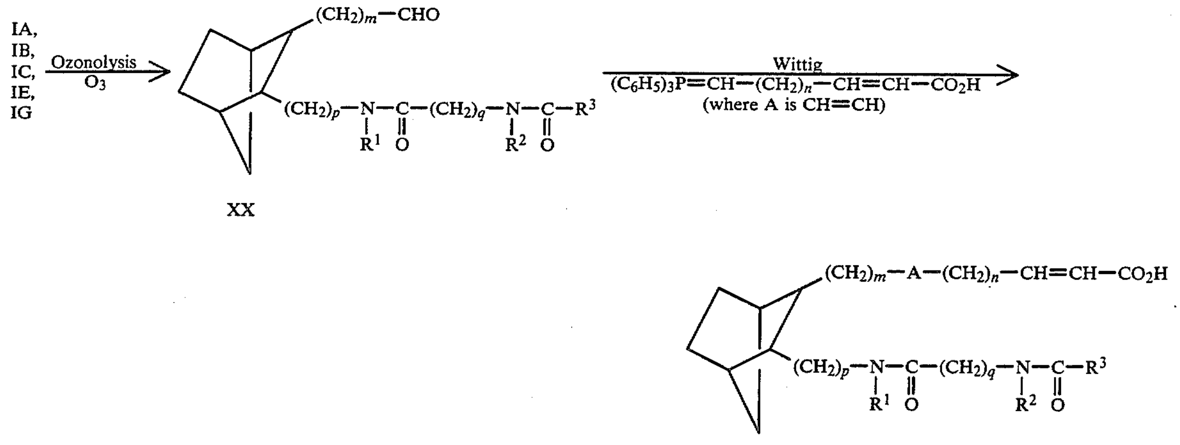
XX
IJ
J. Where Q is 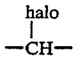 or 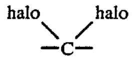
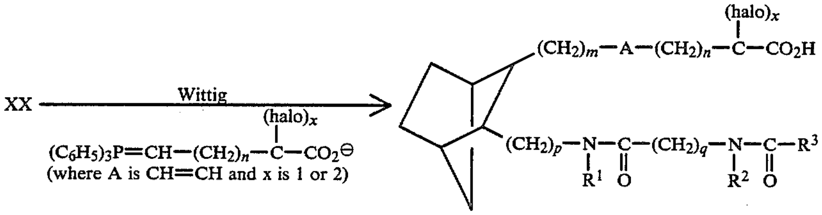
IK
K. Where R is $\overset{\text{O}}{\overset{\|}{\text{C}}}NR^4R^5$ (wherein $R^4$ and $R^5$ are other than hydroxy or alkoxy)
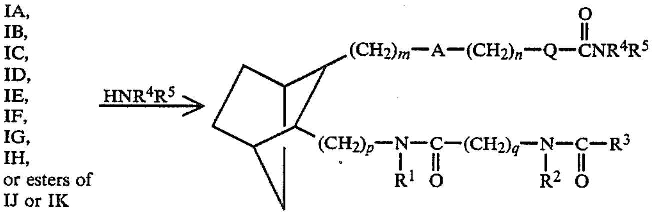
IM
L. Where R is 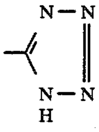 and A is CH=CH
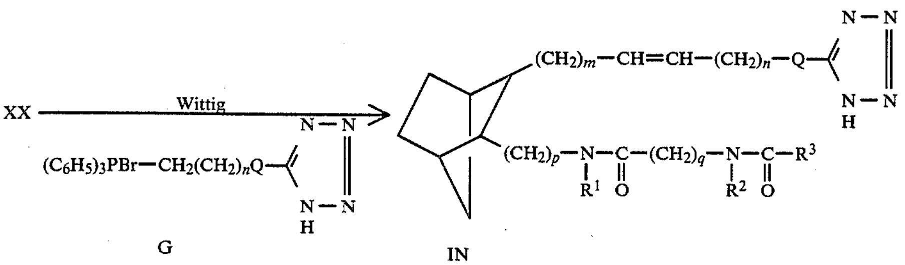
G
IN -continued
M. Where R is 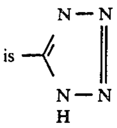 and A is $(CH_2)_2$
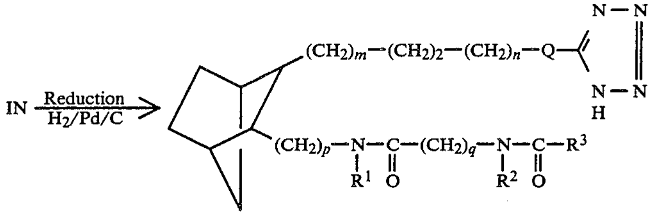
IO
N. Where R is $CH_2OH$
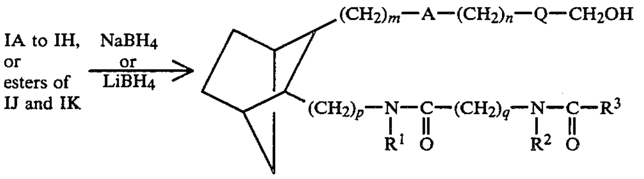
IP
O. Where R is $CO_2H$
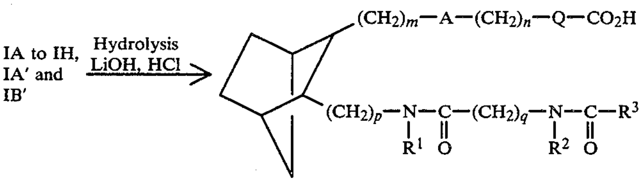
(IQ where A is CH═CH)
(IR where A is $(CH_2)_2$)
P. Where R is 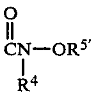
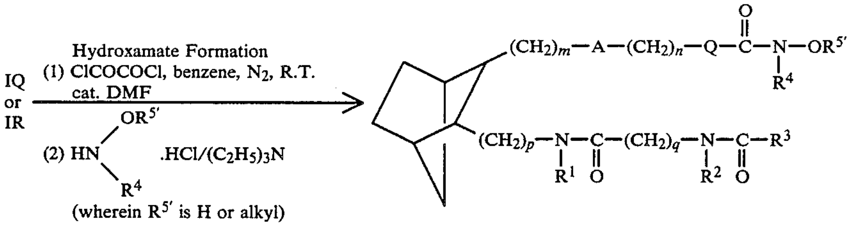
IS
Q. Where $R^3$ is $NH_2$, q = 1
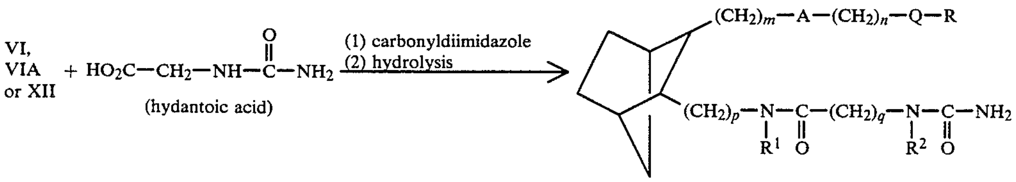
IT As seen in reaction sequence "A", compounds of the invention where Q is $-CH_2-$ or a single bond, p is 1, R is $CO_2$ alkyl, and $R^1$ is H, that is

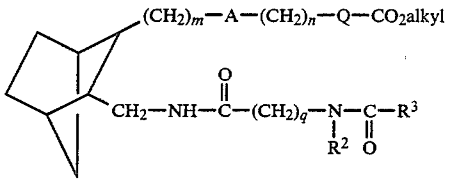

IA are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

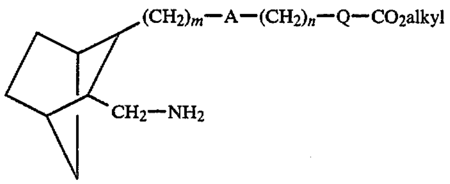

VI

As seen in reaction sequence "A'", where $R^1$ is lower alkyl, an alkylation reaction is carried out as in the reference M. J. O'Donnell et al., *Tetrahedron Lett.* (1984), 25, 3651-3654 to give VIA

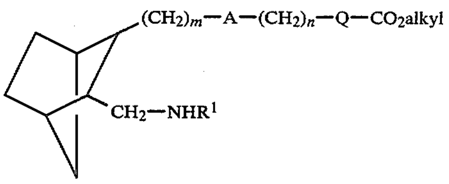

VIA

The amine VI or VIA is then subjected to a CDI coupling reaction by reacting VI or VIA with acid VII

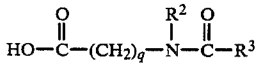

VII in the presence of an inert organic solvent such as tetrahydrofuran and carbonyl diimidazole under an inert atmosphere, such as argon, employing a molar ratio of VI:VII of within the range of from about 1:1 to about 1:1.2, to form the amide ester compound of the invention IA or IA'

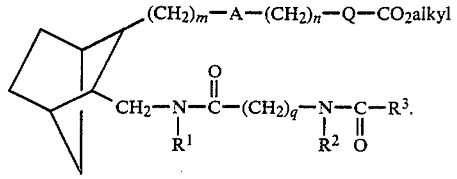

(IA—where $R^1$ is H IA'—where $R^1$ is lower alkyl)

The reaction sequences identified as "B" and "B'" are employed to prepare compounds of the invention wherein Q is $-CH_2-$ or a single bond, p is 2 to 5, and R is $CO_2$ alkyl, that is,

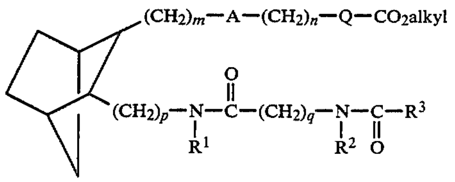

(where p is 2 to 5)

(IB—where $R^1$ is H IB'—where $R^1$ is alkyl)

Compound II or IIA is used to form the aldehyde III (where A is $-CH=CH-$) or IIIA (where A is $-(CH_2)_2$). Thus, to form aldehyde III where A is $-CH=CH-$, compound II is subjected to a Collins oxidation, for example, by reacting II with chromium trioxide in pyridine. To form the aldehyde IIIA (where A is $(CH_2)_2$) compound II is reduced, for example, with hydrogen over a palladium on carbon catalyst, to form hydroxymethyl compound IIA (where A is $(CH_2)_2$) and compound IIA is subjected to a Collins oxidation to form aldehyde IIIA (where A is $(CH_2)_2$). The aldehyde III or IIIA is used to prepare aldehyde IX (where p is 2-5) by carrying out a homologation sequence, such as a Wittig reaction with $C_6H_5)_3P=CHOMe$ followed by hydrolysis, (p—1) times. The aldehyde IX (where p is 2-5) is then carried on to compounds of this invention where p is 2-5, that is

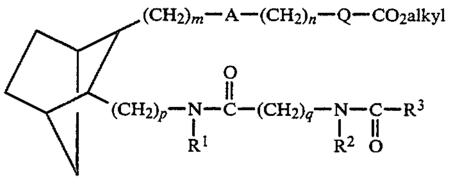

IB (where p is 2 to 5)

by reducing aldehyde IX by reacting with a reducing agent such as sodium borohydride to form alcohol IXA

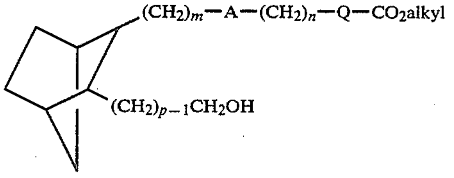

IXA tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

XII

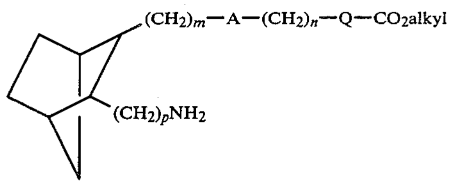

As seen in reaction sequence "B′", where $R^1$ is lower alkyl, an alkylation reaction is carried out as in O'Donnell et al, supra to give XIIA

XIIA

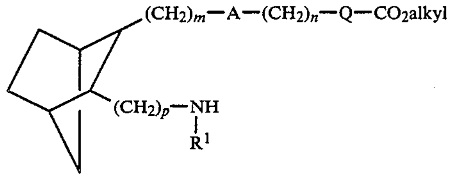

The amine XII or XIIA is then reacted with acid VII in a CDI coupling reaction as described above to form the amide ester compound of the invention IB or IB′

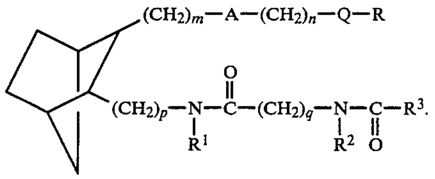

(IB—where $R^1$ is H IB′—where $R^1$ is lower alkyl)

Compounds of the invention wherein m is 2, A is —CH=CH—, p is 1 and Q is $CH_2$ or a single bond may be prepared as outlined in reaction sequence "C" by subjecting starting compound XIII to a Wittig reaction, referred to as Wittig (1), by reacting XIII with an alkoxymethyltriphenyl phosphonium halide, such as (methoxymethyl)triphenylphosphonium chloride, for example, as described in Example 4 of U.S. Pat. No. 4,143,054, to form compound F. The Wittig (1) procedure is repeated on compound F to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II in reaction scheme "A" to form compound IC of the invention.

As seen in reaction sequence "D", compounds of the invention wherein m is 2, A is —$CH_2$—$CH_2$—, p is 1 and Q is $CH_2$ or a single bond may be prepared as outlined in reaction sequence "D" by reducing hydroxymethyl compound XVI to form compound XVIA which is then employed in place of compound IIA in reaction sequence "A" to form compound ID of the invention.

Referring to reaction sequence "E", compounds of the invention wherein m is 3 or 4, A is —CH=CH—, p is 1 and Q is CH or a single bond may be prepared by subjecting aldehyde XIV to the Wittig (1) procedure one time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II in reaction scheme "A" to form compound IE of the invention.

As seen in reaction sequence "F", compounds of the invention wherein m is 3 or 4, A is $CH_2CH$, p is 1 and Q is $CH_2$ or a single bond may be prepared by reducing hydroxymethyl compound XIX to form compound XIXA which is then employed in place of compound II in reaction scheme "A" to form compound IF of the invention.

Thus, compounds of the invention wherein m is 0, 2, 3 or 4 and p is 2, 3 or 4 may be prepared by substituting hydroxymethyl compound XVI, XVIA, XIX, or XIXA in place of hydroxymethyl compound II or IIA in reaction sequences A and B.

Referring now to reaction sequence "G", compounds of the invention wherein m is 0, A is CH=CH, p is 1 and Q is $CH_2$ or a single bond, that is, compound IG may be prepared by subjecting compound XIII (prepared as described in Example 3 of U.S. Pat. No. 4,143,054) to a Wittig reaction, for example, as described in Example 6(c) of U.S. Pat. No. 4,143,054, by reacting B with a carboxyalkyltriphenyl phosphonium halide, such as carboxypentyltriphenyl phosphonium bromide to form the hydroxymethyl compound IXB which may then be used to form the ester IG which, in turn, may be hydrolyzed to the corresponding acid.

As seen in reaction sequence "H", where it is desired to prepare compounds of the invention wherein m is 0 and A is $(CH_2)_2$, the hydroxymethyl compound IXB is reduced by treatment with hydrogen in the presence of a palladium on carbon catalyst to form hydroxymethyl compound IXC which may then be used to form ester IH which then may be hydrolyzed to the corresponding acid.

Referring to reaction sequence "I", compounds of formula I of the invention wherein Q is —CH=CH—, that is IJ

IJ

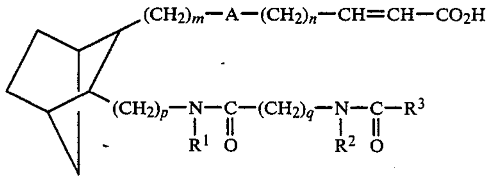

may be prepared by subjecting ester IA, IB, IA′, IB′, IC, IE and IG to ozonolysis by treating IA, IB, IA′, IB′, IC, IE and IG with ozone at −78° C. in methylene chloride and methanol to form aldehyde XX.

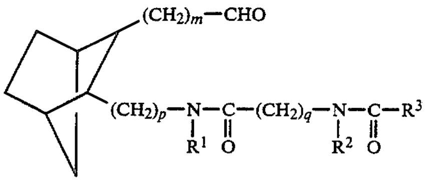
XX which is then treated with Wittig reagent $(C_6H_5)_3P{=}CH{-}(CH_2)_n{-}CH{=}CH{-}CO_2^{\ominus}$ (where A is (—CH=CH—)) to form IJ.

In reaction sequence "J" compounds wherein Q is

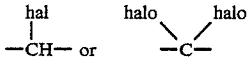

are prepared by subjecting aldehyde XX to a Wittig reaction with

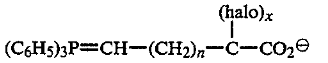
C (where A is CH=CH and x is 1 or 2) to form compounds of the invention IK

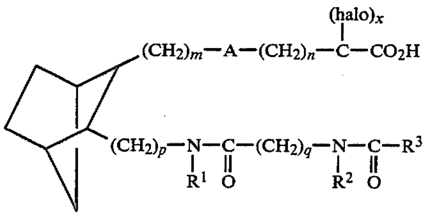
IK

In reaction sequence "K", amides of t he invention of structure IM

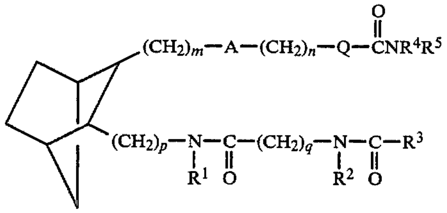
IM wherein $R^4$ and $R^5$ are independently H, alkyl or aryl or prepared by treating ester IA to IH or IL or esters of IJ or IK with an amine of the structure $HNR^4R_5$ E.

Compounds of the invention wherein R is tetrazole

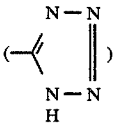

and A is CH=CH are prepared as described in reaction sequence "L" wherin aldehyde XX (prepared as described above) is reacted with a Wittig reagent of the structure G

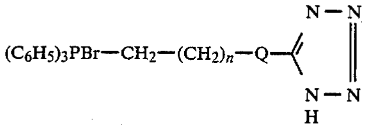
G in the presence of a base, such as potassium t-butoxide or sodium hydride-dimethyl sulfoxide employing a molar ratio of XVII:G of within the range of from about 1:1 to about 0.2:1 to form the compounds of the invention IN where A is —CH=CH—.

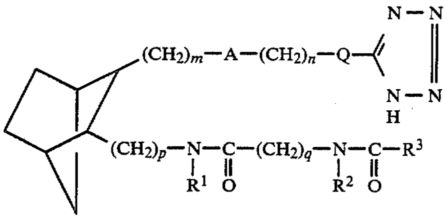
IN

As seen in reaction sequence "M", compound IO may be prepared by reducing compound IN by treating with $H_2$ in the presence of palladium on charcoal.

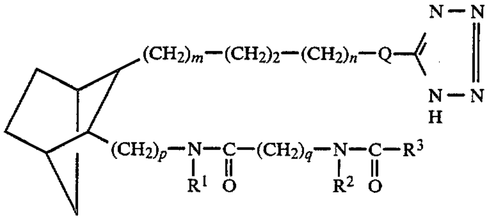
IO

As seen in reaction sequence "N", compounds of the invention wherein R is $CH_2OH$ may be prepared by reducing esters IA to IH, and IL and esters of J and K by treatment with sodium borohydride or lithium borohydride to form compounds of the invention IP

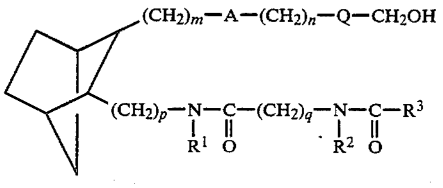
IP

Referring to reaction sequence "O", the esters IA, IA', IB, IB' to IH can be converted to the free acid, that is, to

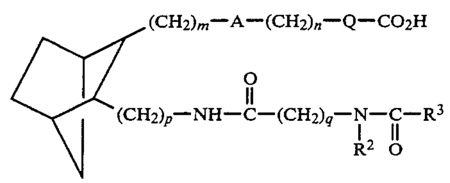

IQ (A is —CH═CH—) IR (A is $(CH_2)_2$)

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IQ and IR.

In the reaction sequence identified as "P" where in Formula I, R is

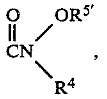

wherein $R^{5'}$ is H or alkyl, a solution of acid dissolved in an inert organic solvent such as benzene is treated with oxalyl chloride and a catalytic amount of dimethylformamide (DMF) and the mixture is stirred at room temperature under nitrogen. The resulting acid chloride is dissolved in an inert organic solvent such as tetrahydrofuran and the so-formed solution is added dropwise into a cold solution of amine hydrochloride H

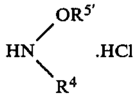

H (wherein $R^{5'}$ is H or alkyl, employing a molar ratio of acid chloride:H of within the range of from about 0.3:1 to about 1:1 and preferably from about 0.5:1) and triethylamine in aqueous tetrahydrofuran to form the hydroxamate IS.

IS

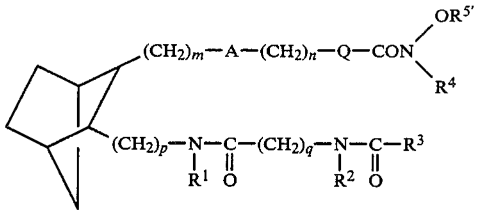

In reaction sequence "Q" compounds of the invention wherein $R^3$ is $NH_2$, q=1, that is IT

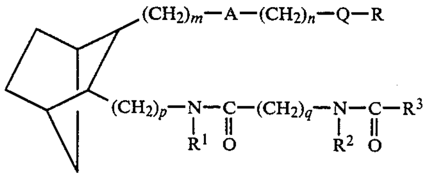

IT may be prepared reacting amine VI, VIA or XII with hydantoic acid in the presence of carbonyldiimidazole and then hydrolyzing the resulting product to form IT.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

To form the sulfinyl and/or sulfonyl analogs of compounds of formula I wherein $R^3$ is -alkyl-S-aryl, alkyl-S-alkyl, or -alkyl-S-alkylaryl, such formula I compounds are subjected to oxidation, for example, by reacting same with sodium periodate or potassium monopersulfate (oxone) in the presence of methanol to form the sulfinyl derivative and/or sulfonyl derivative. Mixtures thereof may be separated by chromatography or other conventional separation procedures.

The starting acid VII

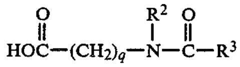

VII may be prepared by reacting the amino acid J

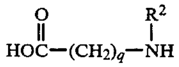

J or its acid chloride with acid chloride K

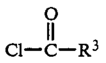

K (or its acid if the acid chloride of J is employed) in the presence of a strong base such as NaOH and water.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

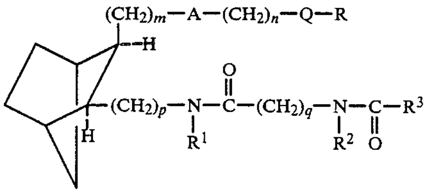

Ia (cis-endo)

-continued

Ib

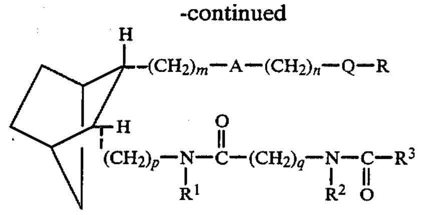

(cis-exo)

Ic

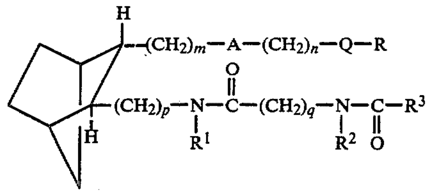

(trans)

Id

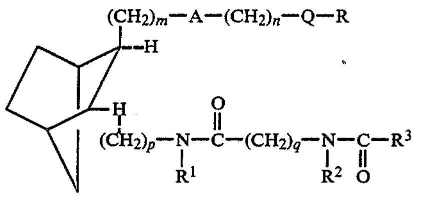

(trans)

The nucleus in each of the compounds of the invention is depicted as

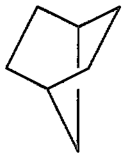

for matter of convenience; it will also be appreciated that the nucleus in the compounds of the invention may be depicted as

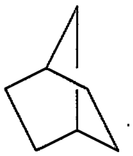

The compounds of this invention are cardiovascular agents useful as platelet aggregation inhibitors, such as in inhibiting arachidonic acid-induced platelet agggregation, e.g., for treatment of thrombotic disease such as coronary or cerebral thromboses, and in inhibiting broncho-constriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1β, 2α(5Z),3α, 4β]-7-[3-[[[[(1-Oxohexyl)amino]acetyl]amino]methyl]-bicyclo[2.2.1]hept-2-yl]-5-heptenoic acid, methyl ester

A. N-Hexanoylglycine

Glycine (7.5 g, 100 mmol) was dissolved in NaOH solution (NaOH:8 g, $H_2O$ 0:50 ml) and cooled to 0° C. $Et_2O$ (50 ml) was added and n-hexanoyl chloride (13.4 g, 100 mmol) was then added dropwise over 60 minutes at 0° C. under vigorous stirring. The reaction was allowed to warm to room temperature and was stirred for 1 hour. 1N-NaOH (10 ml) was added and the layers were separated. The water layer was washed with $Et_2O$ (20 ml ×2). The combined $Et_2O$ layers were extracted with 1N-NaOH (20 ml). The combined water layers were acidified with concentrated HCl to pH 2 and the products were extracted with $Et_2O$ (100 ml×3). The combined $Et_2O$ layers were washed with brine (50 ml) and dried over $MgSO_4$. Filtration and evaporation of solvent gave a colorless solid (16.2 g), which was crystallized from EtOAc (60 ml) to give colorless needle crystals (10.9 g, 63 mmol, 63%), m.p. 93°–96°. TLC: silica gel, MeOH, $CH_2Cl_2$, HCOOH; 10, 89.5, 0.5, PMA $R_f$=0.45.

B. [1β,2α(5Z),3α,4β]-7-3-(Tosyloxymethyl)bicyclo[2.2.1-]hept-2-yl]-5-heptenoic acid, methyl ester Tosyl chloride (4.256 g, 22.4 mmol) dissolved in $CH_2Cl_2$ (30 ml) is added dropwise to a magnetically stirred solution of [lS-[1β,2α(5Z),3α,4β]]-7-[3-(hydroxymethyl)bicyclo[2.2.1]hept-2-yl]-5-heptenoic acid, methyl ester (prepared as described in U.S. Pat. No. 4,542,160 (11.2 mmol) in pyridine (30 ml) at 0° C. After completion of the addition, the reaction is warmed to room temperature and stirred overnight. The reaction is poured into ice/$H_2O$ and stirred for 30 minutes. The products are extracted with EtOAc (80 ml ×3). The combined EtOAc layers are washed with 3N-HCl (40 ml×3), saturated $NaHCO_3$, brine and dried over $MgSO_4$. Filtration and evaporation of solvent gives the corresponding title tosylate.

C.

[1β,2α(5Z),3α,4β]-7-[(3-(Aminomethyl)bicyclo[2.2.-1hept-2-yl]-5-heptenoic acid, methyl ester The title B tosylate is subjected to a Gabriel synthesis to form the corresponding amino compound as described below.

The potassium phthalimide used is purified prior to use by boiling 5 g thereof with 9 ml acetone for 15 minutes, filtering while hot and washing with 5 ml acetone. The remaining solid is dried in vacuo for 6 hours at 100° C. prior to use.

The title B tosylate (19.2 mmol) and purified potassium phthalimide (6.4 g, 34.6 mmol, 1.8 equiv.) in dimethylsulfoxide (70 ml, Burdick & Jackson) are heated at 90°-100° C. for 2½ hours (checked by TLC $Et_2O$ -pet ether 2:1, no tosylate remaining). After cooling to room temperature, water (90 ml) is added. The mixture is poured into ice water (~350 ml) and stirred 30 minutes. The solid is harvested by filtration and washed with more water. The solid is dissolved in warm ethyl acetate (150 ml), washed with water (3×50 ml), dried ($MgSO_4$), filtered and freed of solvent in vacuo. The remaining solid is recrystallized from isopropyl ether to give corresponding phthalimide.

The above phthalimide (13.8 mmol) is dissolved in distilled $CH_2Cl_2$ (24 ml) and distilled ethanol (104 ml) in an argon atmosphere. Anhydrous hydrazine (0.78 ml, 25.6 mmol) is added. The mixture is stirred at room temperature. After 8 hours an additional 0.2 ml of hydrazine is added and the mixture is stirred an additional 15 hours at room temperature. A solid is removed by filtration and washed with more $CH_2Cl_2$. The filtrate is taken to dryness in vacuo (on the pump at end). Cold 0.5 N HCl solution (80 ml) is added. A small amount of solid is removed by filtration and washed with additional 0.5 N HCl solution (80 ml). The acidic solution is washed with ether (2×100 ml) and then basified with solid $K_2CO_3$. The amine is extracted into $CHCl_3$ (3×100 ml), dried ($MgSO_4$) and freed of solvent in vacuo leaving a yellow oil. Ether (100 ml) is added to this oil. After cooling in an ice bath, the solid is removed by filtration. The solvent is removed from the filtrate in vacuo leaving title amine. The material is used without further purification.

D.

1β,2α(5Z),3α,4β]-7-[3-[[[[(1-Oxohexyl)amino]acetyl-]amino]methyl]-bicyclo [2.2.1]hept-2-yl]-5-heptenoic acid, methyl ester Part A compound (1.5 mmol) is dissolved in distilled THF (12 ml) in an argon atmosphere. After cooling in an ice bath carbonyldiimidazole (CDI) (243 mg, 1.5 mmol) is added. The mixture is stirred cold for 1 hour and then at room temperature for 1 hour. The solution is cooled to 0° C. and a solution of Part C amine (1.5 mmol) in THF (3 ml) is added. The mixture is left stirring overnight at room temperature. The solvent is removed in vacuo and the residue is dissolved in $CHCl_3$ (50 ml). This is washed with 1N HCl (20 ml), 1N NaOH (20 ml) and $H_2O$ (20 ml), dried ($MgSO_4$) and freed of solvent in vacuo leaving a viscous oil. The oil is chromatographed on silica gel.

EXAMPLE 2

[1β,2α(5Z),3α,4β]-7-[3-[[[[(1-Oxohexyl)amino]acetyl-]amino]methyl]bicyclo[2.2.1]hept-2-yl]-5-heptenoic acid The Example 1 methyl ester (0.994 mmol) is dissolved in distilled THF (40 ml) and water (8 ml) in an argon atmosphere. 1N LiOH solution (9.5 ml) is added and the mixture is stirred at room temperature for 3¾ hours. After neutralization with 1N HCl (9.5 ml), solid KCl is added and the layers are separated. The aqueous layer is reextracted with $CHCl_3$ (3×50 ml). The combined organic layers (THF+$CHCl_3$) were washed with saturated NaCl solution (2×25 ml), dried ($MgSO_4$), and freed of solvent in vacuo leaving an oil. This is chromatographed on silica gel (30 g, Baker for flash chromatography) eluting with 4% MeOH in $CH_2Cl_2$ to give title acid.

EXAMPLE 3

[1β,2α(5Z),3α,4β]-7-[3-[[[[[(Butylamino)carbonyl-]amino]acetyl]amino]methyl]bicyclo[2.2.1]hept-2-yl]-5-heptenoic acid, methyl ester A. N-[(Butylamino)carbonyl]glycine, ethyl ester Glycine ethyl ester•HCl (5.58 g, 40 mmol) was suspended in distilled $CH_2Cl_2$ (20 ml). After cooling in an ice bath, distilled $Et_3N$ (6.13 ml, 44 mmol) was added. Distilled n-butyl isocyanate (4.95 ml, 44 mmol) was added. The cooling bath was removed and the mixture was left stirring overnight at room temperature. Additional $Et_3N$ (3.05 ml) was added and the mixture was stirred 3 more hours. After diluting with more $CH_2Cl_2$, the solution was washed with water (50 ml), lN HCl (50 ml), saturated $NaHCO_3$ solution (50 ml) and water (50 ml). After drying ($MgSO_4$), the solvent was removed in vacuo leaving the title compound (7.641 g, 94%) which slowly crystallized. This was used without further purification.

B. N-[(Butylamino)carbonyl]glycine

Part A ethyl ester (3.378 g, 16.7 mmol) was dissolved in distilled THF (100 ml) and treated with 1N LiOH solution (40 ml). After stirring overnight at room temperature and acidifying with concentrated HCl, solid KCl was added. The layers were separated. The aqueous layer was reextracted with EtOAc (3×50 ml). The combined organic layers (THF and EtOAc) were washed with saturated NaCl solution (25 ml), dried ($MgSO_4$), and freed of solvent in vacuo leaving the title compound, as a white solid (2.81 g, 97%).

C.

[1β,2α(5Z),3α,4β]-7-[3-[[[[[(Butylamino)carbonyl-]amino]acetyl]amino]methyl]bicyclo[2.2.1]hept-2-yl]-5-heptenoic acid, methyl ester Part B compound (174.2 mg, 1 mmol) is partially dissolved in distilled THF (8 ml) in an argon atmosphere. After cooling in an ice bath, carbonyl diimidazole (CDI) (162 mg, 1 mmol) is added. The mixture is stirred cold 1 hour and at room temperature 1½ hours. The solution is cooled in an ice bath and a solution of chiral amine prepared in Example 1 Part C (1 mmol) in THF (3 ml) is added. The cooling bath is removed and the mixture is left stirring overnight at room temperature. The solvent is removed in vacuo. $CHCl_3$ (35 ml) is added to the residue. The solution is washed with 1N HCl (15 ml), 1N NaOH (15 ml) and $H_2O$ (15 ml), dried ($MgSO_4$) and freed of solvent in vacuo leaving an oil. This is chromatographed on silica gel.

EXAMPLE 4

[1β,2α(5Z),3α,4β]-7-[3-[[[[[(Butylamino)carbonyl-]amino]acetyl]amino]methyl]bicyclo[2.2.1]hept-2-yl]-5-heptenoic acid Example 3 methyl ester (0.491 mmol) is dissolved in distilled THF (20 ml) and water (4.8 ml) in an argon atmosphere. 1N LiOH solution (4.9 ml) is added and the mixture is stirred at room temperature 5 hours. The mixture is neutralized with 1N HCl solution (4.9 ml) and solid KCl is added. The layers are separated. The aqueous layer is reextracted with $CHCl_3$ (3×25 ml). The combined organic layers (THF and $CHCl_3$) are washed with saturated NaCl solution (15 ml), dried ($MgSO_4$) and freed of solvent in vacuo leaving an oil. This is chromatographed on silica gel to give the title compound.

EXAMPLE 5

[1β,2α(5Z),3α,4β]-7-[3-[[[[Methyl(1-oxohexyl-)amino]acetyl]amino]methyl]bicyclo[2.2.1]hept-2-yl]-5-heptenoic acid, methyl ester

A. N-Hexanoyl-N-methylglycine

Sarcosine (1.78 g, 20 mmol) was dissolved in 1N NaOH solution (40 ml) and $Et_2O$ (40 ml) was added. After cooling in an ice bath a solution of hexanoyl chloride (3.1 ml, 22 mmol) in $Et_2O$ (10 ml) was added dropwise. The mixture was stirred cold for 1 hour. The pH was then adjusted to about 8 by adding 1N NaOH solution (about 3 ml) and the mixture was stirred at room temperature 45 minutes. NaOH solution was added to about pH 9–10. The layers were separated and the aqueous layer was washed with $Et_2O$ (50 ml). After acidification of the aqueous layer with concentrated HCl and saturation with solid KCl, the product was extracted into $CHCl_3$ (3×70 ml). The combined $CHCl_3$ extracts were washed with saturated NaCl solution (25 ml), dried ($MgSO_4$), and freed of solvent leaving the title compound as an oil (3.78 g, quant.) which was used without further purification.

B. [1β,2α(5Z),3α,4β]-7-[3-[[[[Methyl(1-oxohexyl-)amino]acetyl]amino]methyl]bicyclo[2.2.1]hept-2-yl]-5-heptenoic acid, methyl ester Part A compound (187 mg, 1 mmol) is dissolved in distilled THF (8 ml) in an argon atmosphere and cooled in an ice bath. Carbonyldiimidazole (CDI) (162 mg, 1 mmol) is added and the mixture is stirred cold for 1 hour and then for 1 hour at room temperature. After cooling in an ice bath, a solution of chiral amine prepared in Example 1 part C (1 mmol) in THF (3 ml) is added. The ice bath is removed and the mixture is stirred overnight at room temperature. The solvent is removed in vacuo. $CHCl_3$ (35 ml) is added to the residue. The solution is washed with 1N HCl (15 ml), 1N NaOH solution (15 ml) and $H_2O$ (15 ml), dried ($MgSO_4$) and freed of solvent in vacuo leaving an oil. This is chromatographed on silica gel to give title compound.

EXAMPLE 6

[1β,2α(5Z),3α,4β]-7-[3-[[[[Methyl(1-oxohexyl-)amino]acetyl]amino]methyl]bicyclo[2.2.1]hept-2-yl]-5-heptenoic acid The Example 5 methyl ester (0.568 mmol) is dissolved in distilled THF (25 ml) and water (5 ml) in an argon atmosphere. 1N LiOH solution is added and the mixture is stirred at room temperature 4 hours. After neutralizing with 1N HCl solution (5.6 ml) and addition of solid KCl, the layers are separated. The aqueous layer is extracted with $CHCl_3$ (3×25 ml). The combined organic layers (THF+$CHCl_3$) are washed with saturated NaCl solution (15 ml), dried ($MgSO_4$) and freed of solvent in vacuo leaving an oil. This is chromatographed on silica gel to give the title compound.

EXAMPLE 7

[1β,2α(5Z),3α,4β]-7-[3-[[[[(Butoxycarbonyl-)amino]acetyl]amino]methyl]bicyclo[2.2.1]hept-2-yl]-5-heptenoic acid, methyl ester

A. N-(Butoxycarbonyl)glycine ethyl ester

Glycine ethyl ester•HCl (3.5 g, 25 mmol) was suspended in distilled $CH_2Cl_2$ (25 ml) in an argon atmosphere. After cooling to −40° C. distilled $Et_3N$ (7.65 ml, 55 mmol) was added followed by dropwise addition of a solution of distilled n-butyl chloroformate (3.2 ml, ~25 mmol) in $CH_2Cl_2$ (10 ml). After stirring at −40° for 1 hour the mixture was left in a freezer (−5° C.) overnight. The mixture was stirred at −5° to −10° for 1 hour. More $CH_2Cl_2$ was added followed by water (50 ml). The layers were separated. The organic layer was washed with 1N HCl (50 ml), saturated $NaHCO_3$ solution (50 ml) and water (50 ml), dried ($MgSO_4$), and freed of solvent in vacuo leaving 3.129 g of material. This was combined with material from a 5 mmol run and chromatographed on silica gel (100 g, Baker for flash chromatography), eluting with ether-hexane 1:1 to give the title compound as an oil (3.196 g, 52.5%). TLC: silica gel, $Et_2O$-hexane 1:1, PMA, $R_f$=0.34.

B. N-(Butoxycarbonyl)glycine

The ethyl ester prepared in part A (3.141 g, 15.47 mmol) was dissolved in 100 ml distilled THF and treated with 1N LiOH solution (40 ml). The mixture was left stirring overnight at room temperature. After acidification with concentrated HCl and addition of solid KCl, the layers were separated. The aqueous layer was reextracted with EtOAc (3×50 ml). The combined organic layers (THF+EtOAc) were washed with saturated NaCl solution (25 ml), dried ($MgSO_4$) and freed of solvent in vacuo leaving the title compound (2.78 g, quant.) which slowly crystallized.

C. [1β,2α(5Z),3α,4β]-7-3-[[[[(Butoxycarbonyl-)amino]acetyl]amino]methyl]bicyclo[2.2.1]hept-2-yl]-5-heptenoic acid, methyl ester The acid prepared in part B (175.2 mg, 1 mmol) is dissolved in distilled THF (8 ml) in an argon atmosphere. After cooling in an ice bath carbonyldiimidazole (CDI) (1 mmol) is added. The mixture is stirred cold 1 hour and at room temperature 1 hour. The mixture is again cooled in an ice bath and a solution of chiral amine (prepared in Example 1 Part C, 1 mmol) in THF (3 ml) is added. The cooling bath is removed and the mixture is left stirring overnight at room temperature. The solvent is removed in vacuo. $CHCl_3$ (35 ml) is added. The solution is washed with 1N HCl (15 ml), 1N NaOH (15 ml) and $H_2O$ (15 ml), dried ($MgSO_4$) and freed of solvent in vacuo. The remaining oil is chromatographed on silica gel to give the title compound.

EXAMPLE 8

[1β,2α(5Z),3α,4β]-7-[3-[[[[(Butoxycarbonyl-)amino]acetyl]amino]methyl]bicyclo[2.2.1]hept-2-yl]-5-heptenoic acid The methyl ester prepared in Example 7 (0.396 mmol) is dissolved in distilled THF (16 ml) and water (3.8 ml) in an argon atmosphere and 1N LiOH solution (3.9 ml) is added. The mixture is stirred at room temperature 5½ hours, then neutralized with 1N HCl solution (3.8 ml). After adding solid KCl the layers are separated. The aqueous layer is reextracted with $CHCl_3$ (3×25 ml). The combined organic layers (THF+$CHCl_3$) are washed with saturated NaCl solution (15 ml), dried ($MgSO_4$) and freed of solvent in vacuo leaving an oil. This is chromatographed on silica gel to give the title compound.

EXAMPLE 9

[1β,2α(5Z),3α,4β]-2,2-Difluoro-7-3-[[[[(1-Oxohexyl-)amino]acetyl]amino]methyl]bicyclo-[2.2.1]hept-2-yl]-5-heptenoic acid

A.

[1β,2α,3α,4β]-2-[3-[[[[(1-Oxohexyl)amino]acetyl-]amino]methyl]bicyclo[2.2.1]hept-2-yl]acetaldehyde $O_3$ is bubbled through a magnetically stirred solution of [1S-[1β,2α(5Z),3α,4β]]-7-[3-[[[[(1-oxohexyl-)amino]acetyl]amino]methyl]bicyclo[2.2.1]hept-2-yl]-5-heptenoic acid, methyl ester (0.5 mmol) (prepared as described in Example 1) in $CH_2Cl_2$/MeOH (10 ml/10 ml) at −78° C., until the solution becomes blue. Excess $O_3$ is then purged by a stream of $N_2$ and $(CH_3)_2S$ (1 ml) is added. The reaction is allowed to warm to room temperature and poured into $CH_2Cl_2$ (50 ml), $H_2O$ (10 ml). The products are extracted into $CH_2Cl_2$ layers. The $H_2O$ layer separated is re-extracted with $CH_2Cl_2$ (30 ml). The combined $CH_2Cl_2$ layers are washed with brine (10 ml) and dried over $MgSO_4$. Filtration and evaporation of solvent gives a crude product which is purified by silica gel column chromatography to afford the title compound.

B. (4-Carboxy-3,3-difluorobutyl)triphenylphosphonium bromide (1) Methyl tetrahydrofuroate Methyl furoate (75 g, 0.595 mole) was dissolved in MeOH (150 ml), and poured into a Parr bottle. Air was replaced with argon, and then 10% Pd/C (2.5 g) was added. The atmosphere was replaced with $H_2$ and methyl furoate was hydrogenated at 40 psi for 48 hours. The reaction was filtered through celite pad, and the pad was washed with ether. The filtrate and the wash were combined and distilled to give the title compound (71 g, 0.546 mole, 59° C./5.1 mmHg, 92%) as a colorless liquid.

(2) Methyl 2-acetoxy-5-bromopentanoate

HBr gas was bubbled into $Ac_2O$ (200 ml) at 0° C. for 2 hours. The specific gravity became 1.4. Part (1) methyl tetrahydrofuroate (70 g, 0.538 mole) was added dropwise under magnetic stirring at 0° C. and the reaction was allowed to warm to room temperature. After stirring overnight, the reaction was poured into ice (~1200 ml) carefully, and left for 30 minutes with occasional swirling. The products were extracted with $Et_2O$ (600 ml×2 and 300 ml). The combined $Et_2O$ layers were washed with dilute NaOH (~0.5%) solution, until the wash became basic. The $Et_2O$ layer was further washed with $H_2O$, dried over $Na_2SO_4$, and filtered. The filtrate was concentrated and distilled to give the title compound (116 g, 0.458 mole, 108° C./1 mmHg, 85%) as a colorless liquid.

(3) Methyl 5-bromo-2-hydroxypentanoate

MeOH (100 ml, distilled over $Mg(OMe)_2$) was saturated with HBr gas at 0° C. This was added to Part (2) compound (60 g, 0.237 mole) in MeOH (200 ml distilled over $Mg(OMe)_2$). The reaction was allowed to warm to room temperature and stirred overnight. The reaction was concentrated in vacuo. Toluene (200 ml) was added to the resulting liquid, and the reaction was concentrated. The same process was repeated twice. The resulting liquid was dissolved in EtOAc (2000 ml) and washed with 0.5% NaOH, brine, and dried over $MgSO_4$. Filtration and evaporation of solvent gave a straw colored oil (44.8 g). This was distilled to give the title compound (34 g, 0.161 mole, 68%) as a colorless liquid.

(4) Methyl 5-bromo-2-oxopentanoate

Jones' reagent ($CrO_3$:9.58 g, $H_2SO_4$: 8.47 ml, $H_2O$:36.8 ml) was added to a magnetically stirred solution of Part (3) compound (12.53 g, 59.3 mmole) in acetone (150 ml) at room temperature. The addition was controlled to maintain the temperature below 35° C. After the completion of the addition, the reaction was stirred at room temperature for 45 minutes. Isopropyl alcohol (30 ml) was added dropwise and stirred for 30 minutes. The reaction was then diluted with $H_2O$ (500 ml) and the products were extracted with $CH_2Cl_2$ (1 1.). The $CH_2Cl_2$ layer was washed with brine (100 ml×3) and dried over $MgSO_4$. Filtration and evaporation of solvents gave the title compound (11.4 g, 54.5 mmole, 92%) as a colorless liquid.

(5) Methyl 5-bromo-2,2-difluoropentanoate

Part (4) compound (11.4 g, 54.5 mmole) was added dropwise to $(C_2H_5)_2$ $NSF_3$ (DAST) (6.8 ml, 55.7 mmole) at room temperature. The container of Part (4) was rinsed with $CH_2Cl_2$ (20 ml), which was added to the reaction. The reaction was stirred at room temperature for 1 hour and poured into $H_2O$ (80 ml). The products were extracted with $CH_2Cl_2$ (40 ml×3). The combined $CH_2Cl_2$ layers were washed with $H_2O$ (20 ml×3) and dried over $MgSO_4$. Filtration and evaporation of solvent gave a straw colored liquid (10.8 g). This was distilled to give the title compound (8.4 g, 36.3 mmole, 67%, 41° C./0.015 mmHg) as a colorless liquid.

(6) 5-Bromo-2,2-difluoropentanoic acid

HBr gas was introduced into 48% HBr in $H_2O$ (100 ml) with occasional cooling in an ice bath until the weight became 180 g. The HBr solution was then added to Part, (5) compound (8.4 g, 36.3 mmole) at room temperature and the reaction was stirred for 5 hours at room temperature. The reaction was cooled to 0° C. and poured into $Et_2O$ (900 ml) in an ice bath. The products were extracted into the $Et_2O$ layer. The water layer was further extracted with $Et_2O$ (200 ml and 100 ml). The combined ether layers were washed with $H_2O$ (200 ml). The $H_2O$ wash was backwashed with $Et_2O$ (100 ml). The $Et_2O$ layers were combined and dried over $MgSO_4$. Filtration and evaporation of solvent gave the title compound (7.8 g, quant.) as a colorless liquid.

(7)
(4-Carboxy-4,4-difluorobutyl)triphenylphosphonium bromide

Acetonitrile (23 ml) was added to a mixture of triphenylphosphine (6.7 g, 25.7 mmole) and Part (6) compound (4.6 g, 21.2 mmole). The solution was heated at gentle reflux under magnetic stirring for 30 hours. Toluene (46 ml) was then added and the reaction was brought to reflux for a brief period. The reaction was allowed to cool to 5° C. and kept overnight. The resulting white precipitates were collected, washed with cold acetonitrile/toluene (½), and dried in a heated vacuum oven (60° C.~5 mmHg) to give the title bromide (9.8 g, 20.4 mmole, 96.5%) as white solid.

C.
[1β,2α(5Z),3α,4β]-2,2-Difluoro-7-[3-[[[[(1-oxohexyl-)amino]acetyl]amino]-methylbicyclo[2.2.1]hept-2-yl]-5-heptenoic acid (4-Carboxy-4,4-difluorobutyl)triphenylphosphonium bromide (1.27 g) (prepared in Part B) is suspended in THF (15 ml). KOt-Amylate (1.7 M in toluene, 3 ml) is added at room temperature. The reaction is stirred for 4 hours. The resulting solution is transferred dropwise to aldehyde obtained in Part A, (250 mg) in THF (10 ml) at 0° C. The reaction is warmed to room temperature and stirred for 15 hours. Saturated $NH_4Cl$ (25 ml) is added and the products are extracted with EtOAc (40 ml×3). The combined organic layers are washed with brine (30 ml) and dried over $MgSO_4$. Filtration and evaporation of solvents afford an oil, which is purified by silica gel column to give the title compound.

EXAMPLE 10

[1β,2α(2E,5Z)3α,4β]-7-[3-[[[[(1-Oxohexyl)-amino]acetyl]amino]methyl]bicyclo[2.2.1]hept-2-yl]-2,5-heptadienoic acid (4-Carboxy-2-butenyl)triphenylphosphonium bromide (1.13 g) is suspended in THF (15 ml). KOt Amylate (1.7 M in toluene, 3 ml) is added at room temperature. The reaction is stirred for 4 hours. The resulting solution is transferred dropwise to aldehyde obtained in Example 9 Part A, (250 mg) in THF (10 ml) at 0° C. The reaction is warmed to room temperature and stirred for 15 hours. Saturated $NH_4Cl$ (25 ml) is added and the products are extracted with EtOAc (40 ml×3). The combined organic layers are washed with brine (30 ml) and dried over $MgSO_4$. Filtration and evaporation of solvents afford a crude product, which is purified by silica gel column to give the title compound.

EXAMPLE 11

[1β,2α(5Z),3α,4β]-N-Methyl-7-[3-[[[[(1-Oxohexyl-)amino]acetyl]amino]methyl]bicyclo-[2.2.1]hept-2-yl]-5-heptenamide 40% $MeNH_2$ in $H_2O$ (2 ml) is added to a magnetically stirred solution of ester prepared in Example 1 (400 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 12

[1β,2α(5Z),3α(R),4β]-7-[3-[[[1-Oxo-2-[(1-Oxohexyl-)amino]propyl]amino]methyl]bicyclo-[2.2.1]hept-2-yl]-5-heptenoic acid, methyl ester A. (2R)-2-(Hexanoylamino)propionic acid D-alanine (20 mmol) and hexanoyl chloride (22 mmol) were reacted using the method as described in Example 5 Part A to give the title compound as a white crystalline material (2.45 g, 65.5%) after recrystallization from isopropyl ether (20 ml), m.p. 82°-95° C.

B.
[1β,2α(5Z),3β(R),4β]-7-[3-[[[1-Oxo-2-[(1-Oxohexyl-)amino]propyl]amino]-methyl]bicyclo[2.2.1]hept-2-yl]-5-heptenoic acid, methyl ester Part A acid compound (1 mmol) and chiral amine prepared as described in Example 1 Part C (1 mmol) are coupled using CDI (1 mmol) as described in Example 5 Part B. The crude product is chromatographed on silica gel to give the title methyl ester.

EXAMPLE 13

1β,2α(5Z),3α(R),4β]-7-[3-[[[1-Oxo-2-[(1-Oxohexyl-)amino]propyl]amino]methyl]bicyclo-[2.2.1]hept-2-yl]-5-heptenoic acid The Example 12 methyl ester (0.49 mmol) is hydrolyzed with LiOH solution in a THF-water mixture as described in Example 6. The crude product is chromatographed on silica gel to give the title acid.

EXAMPLE 14

[1β2α(5Z),3α(S),4β]-7-[3-[[[1-Oxo-2-[(1-oxohexyl-)amino]propyl]amino]methyl]bicyclo-[2.2.1]hept-2-yl]-5-heptenoic acid, methyl ester A. (2S)-2-(Hexanoylamino)propionic acid L-Alanine (10 mmol) and hexanoyl chloride (11 mmol) were reacted using the method described in Example 5 Part A to give the title compound as a white crystalline material (1.091 g, 58%) after recrystallization from isopropyl ether (~6 ml).

B. [1β, 2α(5Z),3α(S),4β]-7-[3-[[[1-Oxo-2-[(1-oxohexyl)amino]propyl]amino]-methyl]bicyclo[2.2.1hept-2-yl]-5-heptenoic acid, methyl ester Part A compound (1 mmol) and chiral amine (prepared as described in Example 1 Part C) (1 mmol) are coupled using CDI (1 mmol) as described in Example 5 Part B. The crude product is chromatographed on silica gel (Baker for flash chromatography) give the title methyl ester.

EXAMPLE 15

[1β2α(5Z),3α(S),4β]-7-3-[[[1-Oxo-2-[(1-oxohexyl-)amino]propyl]amino]methyl]bicyclo-[2.2.1]hept-2-yl]-5-heptenoic acid The Example 14 methyl ester (0.40 mmol) is hydrolyzed with LiOH in a THF-water mixture as described in Example 6 and purified by silica gel chromatography.

EXAMPLE 16

[1$\beta$,2$\alpha$(5Z),3$\alpha$,4$\beta$]-7-[3-[[[2-Methyl-2-[(1-Oxohexyl-)amino]-1Oxohexyl)amino]-1-oxopropyl]amino]methyl]-bicyclo[2.2.1]hept-2-yl]-5-heptenoic acid, methyl ester A. 2-(Hexanoylamino)-2-methylpropionic acid 2-Aminoisobutyric acid (2.0 g, 19.4 mmol) and n-hexanoyl chloride (3.0 g, 22.4 mmol) were reacted in the presence of NaOH (1.6 g, 40 mmol) in a mixture of ether and water using the method described in Example 5, Part A. The title compound (1.90 g, 49%) was obtained after crystallization from benzene, m.p. 141°–143° C.

B. [1$\beta$, 2$\alpha$(5Z),3$\alpha$, 4$\beta$]-7-[3-[[[2-Methyl-2-[(1-Oxohexyl)amino]-1-oxopropyl]amino]methyl]bicyclo-[2.2.1]hept-2-yl-5-heptenoic acid, methyl ester Part A compound (1 mmol) is reacted with CDI (1 mmol) and then with chiral amine prepared as described in Example 1 Part C (1 mmol) employing the method described in Example 1 Part D. The crude product is chromatographed on silica gel to give title ester.

EXAMPLE 17

[1$\beta$,2$\alpha$(5Z),3$\alpha$,4$\beta$]-7-[3-[[[2-Methyl-2-[(1-oxohexyl-)amino]-1oxopropyl]amino]methyl]-bicyclo[2.2.1]hept-2-yl]-5-heptenoic acid The Example 16 methyl ester (0.51 mmol) is hydrolyzed with LiOH in a water-THF mixture as described in Example 6. The product is chromatographed on silica gel to give title acid.

EXAMPLE 18

[1$\beta$,2$\alpha$(5Z),3$\alpha$,4$\beta$]-7-3-[[[[(1-Oxoheptyl)-amino]acetyl-]amino]methyl]bicyclo[2.2.1]-hept-2-yl]-5-heptenoic acid, methyl ester A. 2-(Heptanoylamino)acetic acid Glycine (1.5 g, 20 mmol) and heptanoyl chloride (22 mmol) were reacted in the presence of NaOH (40 mmol) in a mixture of water and ether using the method described in Example 5. The crude product was recrystallized from EtOAc (30 ml) to give title compound (2.71 g, 72%), m.p. 98°–100° C.

B. [1$\beta$,2$\alpha$(5Z),3$\alpha$,4$\beta$]-7-[3-[[[[(1-Oxoheptyl)amino]acetyl-]amino]methyl]-bicyclo[2.2.1]hept-2-yl]-5-heptenoic acid, methyl ester Part A compound (1 mmol) is reacted with CDI (1 mmol) and then with chiral amine (1 mmole) prepared as described in Example 1 Part C employing the method described in Example 5 Part B. The crude product is chromatographed on silica gel.

EXAMPLE 19

[1$\beta$2$\alpha$(5Z),3$\alpha$,4$\beta$]-7-[3-[[[[(1-Oxoheptyl)-amino]acetyl-]amino]methyl]bicyclo[2.2.1]-hept-2-yl]-5-heptenoic acid The Example 18 methyl ester (0.607 mmol) is hydrolyzed with LiOH in a water-THF mixture as described in Example 6.

EXAMPLE 20

[1$\beta$,2$\alpha$,3$\alpha$,4$\beta$)-7-[3-[[[[(1-Oxohexyl)amino]-acetyl-]amino]methyl]bicyclo[2.2.1]hept-2-yl]-heptanoic acid, methyl ester A. (1$\beta$,2$\alpha$,3$\alpha$,4$\beta$)-7-[3-(Hydroxymethyl)bicyclo[2.2.1-]hept-2-yl]-heptanoic acid, methyl ester To 800 mg (3.0 mmole) of the [1$\beta$,2$\alpha$(Z),-3$\alpha$,4$\beta$]-7-[3-(hydroxymethyl)bicyclo[2.2.1]-hept-2-yl]-5-heptenoic acid, methyl ester dissolved in 120 ml of ethyl acetate is added, under an argon atmosphere, 160 mg of 5% Pd on carbon. The argon atmosphere is exchanged for a slight positive pressure of hydrogen and the reaction is stirred for 8 hours at 25°, filtered through a celite plug and evaporated to provide the title A compound.

B. (1$\beta$,2$\alpha$,3$\alpha$,4$\beta$)-7-[3-[[[[(1-Oxohexyl)-amino]acetyl-]amino]methyl]bicyclo-[2.2.1]hept-2-yl]heptanoic acid, methyl ester Following the procedure of Example 1 except substituting the Part A alcohol-ester for the alcohol ester employing in Example 1 Part B, the title product is obtained.

EXAMPLE 21

1$\beta$,2$\alpha$(5Z),3$\alpha$,4$\beta$]-7-[3-[[[(1-Oxo-3-[(1-oxopentyl-)amino]propyl]amino]methyl]bicyclo-[2.2.1]hept-2-yl]-5-heptenoic acid, methyl ester A. 3-(Pentanoylamino)propionic acid $\beta$-Alanine (20 mmol) was reacted with valeryl chloride (22 mmol) in the presence of NaOH (40 mmol) in a mixture of $H_2O$ and ether using the method described in Example 5. The crude crystalline product (2.75 g, 79%) was recrystallized from a mixture of isopropyl ether (150 ml) and ethyl acetate (10 ml) to give title acid (1.51 g, 44%), m.p. 73°–76° C.

B. [1$\beta$,2$\alpha$(5Z),3$\alpha$,4$\beta$]-7-3-[[[(1-Oxo-3-[(1-oxopentyl-)amino]propyl]amino]-methyl]bicyclo[2.2.1]hept-2-yl]-5-heptenoic acid, methyl ester Part A acid (1 mmol) is reacted with carbonyl diimidazole (1 mmol) followed by [1$\beta$,2$\alpha$(5Z),3$\alpha$,4$\beta$]-7-[3-(aminomethyl)-bicyclo[2.2.1hept-2-yl]-5-heptenoic acid, methyl ester (prepared as described in Example 1 Part C (1 mmole)). The crude product is chromatographed on silica gel to give title product.

EXAMPLE 22

[1$\beta$,2$\alpha$(5Z),3$\alpha$,4$\beta$]-7-[3-[[[1-Oxo-3-[(1-oxopentyl-)amino]propyl]amino]methyl]bicyclo-[2.2.1]hept-2-yl]-5-heptenoic acid The Example 21 methyl ester (0.71 mmol) is hydrolyzed with LiOH in a THF-$H_2O$ mixture as described in Example 6.

EXAMPLE 23

[1$\beta$,2$\alpha$(5Z),3$\alpha$,4$\beta$]-7-[3-[[[[(4-Phenylbenzoyl)-amino]acetyl]amino]methyl]bicyclo[2.2.1]-hept-2-yl]-5-heptenoic acid, methyl ester A. 2-[(4-Phenylbenzoyl)amino]acetic acid Glycine (5 mmol) was reacted with 4-biphenylcarbonyl chloride (about 5 mmol) in the presence of 1N NaOH solution (10 ml), ether (21 ml) and THF (2 ml) using the procedure described in Example 5. Most of the product precipitated as a solid on acidification of the aqueous layer during the work up. This was found to be quite insoluble in $CHCl_3$ and EtOAc. It was largely dissolved in $CH_3CN$ (~35 ml) and filtered to remove insoluble material. Crystalline acid (0.81 g, 63%) was deposited on cooling, m.p. 207°-218° C. decomp.

B.

[1β,2α(5Z),3α,4β]-7-[3-[[[[(4-Phenylbenzoyl-)amino]acetyl]amino]-methyl]bicyclo[2.2.1hept-2-yl]-5-heptenoic acid, methyl ester Part A acid (1 mmol) is reacted with carbonyldiimidazole (1 mmole) followed by 1β,2α(5Z),3α,4β]-7-[3-(aminomethyl)bicyclo-[ 2.2.1]hept-2-yl]-5-heptenoic acid, methyl ester (1 mmole) as in Example 1, Part C. After stirring overnight at room temperature, DMF is added and the mixture is left stirring an additional 24 hours. After the usual work up, the product is chromatographed on silica gel to give title ester.

EXAMPLE 24

[1β,2α(5Z),3α,4β]-7-[3-[[[[(4-Phenylbenzoyl)-amino]acetyl]amino]methyl]bicyclo[2.2.1]-hept-2-yl]-5-heptenoic acid The Example 23 methyl ester (0.279 mmol) is hydrolyzed with LiOH as described in Example 6.

EXAMPLE 25

(1β,2α,3α,4β)-7-[3-[[[[2-Methyl-2-[(1-oxohexyl)amino]-1-oxopropyl]amino]methyl]-bicyclo[2.2.1]hept-2-yl]heptanoic acid Following the procedure of Example 2 except substituting the Example 16 Part A acid for the Example 1 Part A acid, the title acid is obtained.

EXAMPLE 26

[1β,2α(5Z),3α,4β]-7-[3-[[[[(1-Oxopropyl)amino]-acetylamino]methyl]bicyclo[2.2.1]hept-2-yl]-5-heptenoic acid Following the procedure of Examples 1 and 2 except substituting propanoyl chloride for hexanoyl chloride, the title compound is obtained.

EXAMPLE 27

[1β,2α(5Z),3α,4β]-7-[3-[[[[(1-Oxoethyl)amino]-acetyl-]amino]methyl]bicyclo[2.2.1]hept-2-yl]-5-heptenoic acid Following the procedure of Examples 1 and 2 except substituting acetyl chloride for hexanoyl chloride, the title compound is obtained.

EXAMPLE 28

1β,2α(5Z),3α,4β]-7-[3-[[[[(1-Oxo-2-butenyl)-amino]acetyl]amino]methyl]bicyclo[2.2.1]hept-2-yl]-5-heptenoic acid Following the procedure of Examples 1 and 2 except substituting 2-butenoyl chloride for hexanoyl chloride, the title compound is obtained.

EXAMPLE 29

[1β,2α(5Z),3α,4β]-7-[3-[[[[(1-Oxo-3-butynyl)-amino]acetyl]amino]methyl]bicyclo-2.2.1]hept-2yl]-5-heptenoic acid Following the procedure of Examples 1 and 2 except substituting 3-butynoyl chloride for hexanoyl chloride, the title compound is obtained.

EXAMPLE 30

[1β,2α(5Z),3α,4β]-7-[3-[[[(Pentyl]amino)-carbonylamino]acetyl]amino]methyl]bicyclo-[2.2.1]hept-2-yl]-5-heptenoic acid Following the procedure of Examples 3 and 4 except substituting n-pentyl isocyanate for n-butyl isocyanate, the title compound is obtained.

EXAMPLE 30A

[1β,2α(5Z),3α,4β]-7-[3-[[[[[(Phenylamino)-carbonyl-]amino]acetyl]amino]methyl]bicyclo-[2.2.1]hept-2-yl]-5-heptenoic acid Following the procedure of Examples 3 and 4 except substituting phenyl isocyanate for n-butyl isocyanate, the title compound is obtained.

EXAMPLE 31

[1β,2α(5Z),3α,4β]-7-[3-[[[[(Phenylcarbonyl)-amino]acetyl]amino]methyl]bicyclo[2.2.1]hept-2-yl]-5-heptenoic acid Following the procedure of Examples 1 and 2 except substituting benzoyl chloride for hexanoyl chloride, the title compound is obtained.

EXAMPLE 32

[1β,2α(5Z),3α,4β]-7-[3-[[[1-Oxo-3-[ethyl(phenylcarbonyl)amino]propyl]amino]methyl]-bicyclo[2.2.1]hept-2-yl]-5-heptenoic acid Following the procedure of Examples 5 and 6 except substituting 3-(ethylamino)propionic acid for sarcosine and benzoyl chloride for hexanoyl chloride, the title compound is obtained.

EXAMPLE 33

[1β,2α(5Z),3α,4β]-7-[3-[[[[(Benzyloxycarbonyl)-amino]acetyl]amino]methyl]bicyclo[2.2.1]hept-2-yl]-5-heptenoic acid Following the procedure of Examples 7 and 8 except substituting benzyl chloroformate for n-butyl chloroformate, the title compound is obtained.

EXAMPLE 34

(1β,2α,3α,4β)-7-[3-[[[[(1-Oxobutyl)amino]-acetylamino]methyl]bicyclo[2.2.1]hept-2-yl]-heptanoic acid Following the procedure of Example 20 except substituting butanoyl chloride for hexanoyl chloride, the title compound is obtained.

EXAMPLE 35

(1β,2α,3α,4β)-7-[3-[[[[(1-Oxo-2-propenyl)-amino]acetyl]amino]methyl]bicyclo[2.2.1]hept-2-yl]heptanoic acid Following the procedure of Example 20 except substituting propenyl chloride for hexanoyl chloride, the title compound is obtained.

EXAMPLE 36

(1β,2α,3α,4β)-7-[3-[[[[(1-Oxo-4-pentynyl)-amino]acetyl]amino]methyl]bicyclo[2.2.1]hept-2-yl]heptanoic acid Following the procedure of Example 20 except substituting 4-pentynoyl chloride for hexanoyl chloride, the title compound is obtained.

EXAMPLE 37

(1β,2α,3α,4β)-7-[3-[[[[[(Phenylamino)carbonyl]-amino]acetyl]amino]methyl]bicyclo[2.2.1]-hept-2-yl]heptanoic acid Following the procedure of Examples 20 and 3 except substituting phenyl isocyanate for n-butyl isocyanate in Example 3 Part A, the title compound is obtained.

EXAMPLE 38

(1β,2α,3α,4β)-7-[3-[[[1-Oxo-4-propyl(1-oxobenzyl-)amino]butyl]amino]methyl]bicyclo[2.2.1]-hept-2-yl]heptanoic acid Following the procedure of Examples 20 and 5 except substituting 4-(propylamino)butanoic acid for sarcosine in Example 5 Part A, the title compound is obtained.

EXAMPLE 39

(1β,2α,3α,4β)-7-[3-[[[[(Benzyloxycarbonyl)-amino]acetyl]amino]methyl]bicyclo[2.2.1]hept-2-yl]heptanoic acid Following the procedure of Examples 20 and 7 except substituting benzyl chloroformate for n-butyl chloroformate, the title compound is obtained.

EXAMPLE 40

[1β,2α(5Z),3α,4β]-7-[3-[2-[[[(1-Oxohexyl)amino]-acetyl]amino]ethyl]bicyclo[2.2.1]hept-2-yl]-5-heptenoic acid

A.

[1β,2α(Z),3α,4β]-7-[3-(2-Oxo)ethyl-bicyclo[2.2.1]hept-2-yl-5-heptenoic acid, methyl ester Into a dry 100 ml round bottom 3-necked flask containing a stir bar is added dried 12.9 g (37.7 mmoles) methoxymethyltriphenylphosphonium chloride ($(C_6H_5)_3P^+—CH_2OCH_3Cl^-$) and 235 ml distilled toluene (stored over molecular sieves). The resulting suspension is stirred in an ice-bath, under argon, until cold and than a 1.55 M solution of 18.3 ml (28.3 mmol) of potassium t-amylate in toluene is added dropwise. A bright red solution formed which is stirred at 0° C. for an additional 35 minutes. Thereafter, a solution of 18.8 mmol of [1β,2α(5Z),3α,4β]-7-[3-formyl]bicyclo[2.2.1]-hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated $NH_4Cl$, and extracted with ether (4×200 ml). The combined ether phases are washed with NaCl, saturated solution, and dried ($MgSO_4$) and concentrated to yield an oil in a white crystalline solid (phosphine oxide). The white solid is triturated with EtOAc and the mother liquor is purified by chromatography on an LPS-1 silica column. The fractions obtained are (A) [1β,2α(Z),3α,4β]-7-[3-(2-oxo)ethylbicyclo[2.2.1]hept-2-yl]-5-heptenoic acid, methyl ester, (B) [1β,2α(5Z),3α,4β]-7-[3-(2-methoxy)-ethenylbicyclo2.2.1]hept-2-yl]-5-heptenoic acid, methyl ester, and (C) [1α,2(Z),3α, 4β]-7-[3-(2,2-dimethoxy)ethylbicyclo[2.2.1]-hept-2-yl]-5-heptenoic acid, methyl ester.

Compounds (B) and (C) are each treated with trifluoroacetic acid to convert each to compound (A).

B.

[1β,2α(5Z),3α,4β]-7-[3-(2-Hydroxyethyl)bicyclo[2.2.1-]hept-2-yl]-5-heptenoic acid, methyl ester The aldehyde (5 mmol) from part A in methanol (50 ml) is treated with $NaBH_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated $KHCO_3$, saturated NaCl and dried ($MgSO_4$). The ether is evaporated to yield the title B compound.

C.

[1β,2α(Z),3α,4β]-7-[3-[2-[[[(1-Oxohexyl)amino]acetyl-]amino]ethyl]-bicyclo[2.2.1]hept-2-yl]-5-heptenoic acid Following the procedure of Examples 1 and 2 except substituting the above part B alcohol for the alcohol used in Example 1 Part B, the title compound is obtained.

EXAMPLE 41

(1β,2α,3α,4β)-7-[3-[2-[[[(1-Oxohexyl)amino]-acetyl-]amino]ethyl]bicyclo[2.2.1]hept-2-yl]-heptanoic acid Following the procedure of Examples 40 and 1 except substituting (1β,2α,3α,4β)-7-[3-formylbicyclo[2.2.1]hept-2-yl]heptanoic acid, methyl ester for [1β,2α(Z),3α,4β]-7-[3-formylbicyclo-[2.2.1]hept-2-yl]-5-heptenoic acid, methyl ester, the title compound is obtained.

EXAMPLE 42

[1β,2α(5Z),3α,4β]-7-[3-[2-[[[(1-Oxopropyl)amino]-acetyl]amino]ethyl]bicyclo[2.2.1]hept-2-yl]-5-heptenoic acid Following the procedure of Example 40 except substituting propionoyl chloride for hexanoyl chloride, the title compound is obtained.

EXAMPLE 43

(1β,2α,3α,4β)-7-[3-[2-[[[(1-Oxo-2-butenyl)amino]-acetyl]amino]ethyl]bicyclo[2.2.1]hept-2-yl]-heptanoic acid Following the procedure of Examples 40 and 23 except substituting 2-butenoyl chloride for hexanoyl chloride, the title compound is obtained.

EXAMPLE 44

[1β,2α(5Z),3α,4β]-7-[3-[2-[[[(Phenylamino)-carbonyl]amino]acetyl]amino]ethyl]bicyclo-[2.2.1]hept-2-yl]-5-heptenoic acid Following the procedure of Examples 40 and 3 except substituting phenyl isocyanate for n-butyl isocyanate, the title compound is obtained.

EXAMPLE 45

[1β,2α(5Z),3α,4β]-7-[3-[2-[[1-Oxo-3-[ethyl(1-oxophenylmethy)amino]propyl]amino]ethyl]-bicyclo[2.2.1]hept-2-yl]-5-heptenoic acid Following the procedure of Examples 40 and 5 except substituting 3-(ethylamino)propionic acid for sarcosine and benzoyl chloride for hexanoyl chloride, the title compound is obtained.

EXAMPLE 46

[1β,2α(5Z),3α,4β]-7-[3-[4-[[[(1-Oxohexyl)-amino]acetyl]amino]butyl]bicyclo[2.2.1]-hept-2-yl]-5-heptenoic acid

A.

[1β,2α(5Z),3α,4β]-7-3-[(3-Oxo)-propyl]bicyclo[2.2.1]hept-2-yl]-5-heptenoic acid, methyl ester Following the procedure of Example 40 Part A except substituting [1β,2α(Z),3α,4β]-7-[3-(2-oxo)-ethylbicyclo[2.2.1]hept-2-yl]-5heptenoic acid, methyl ester for [1β,2α(Z),3α,4β]-7-[3-formylbicyclo2.2.1]hept-2-yl]-5-heptenoic acid, methyl ester, the title A compound is obtained.

B.

[1β,2α(Z),3α,4β]-7-[3-[(4-Oxo)-butyl]bicyclo[2.2.1]hept-2-yl]-5-heptenoic acid, methyl ester Following the procedure of Example 40 Part A except substituting the aldehyde from Part A above for [1β,2α(Z),3α,4β-7-[3-formylbicyclo[2.2.1]-hept-2-yl]-5-heptenoic acid, methyl ester, the title B compound is obtained.

C.

[1β,2α(Z),3α,4β]-7-[3-(4-Hydroxybutyl)bicyclo[2.2.1]hept-2-yl]-5-heptenoic acid, methyl ester Following the procedure of Example 40 Part B except substituting the title B aldehyde for [1β,2α(Z),3α,4β]-7-[3-(2-oxo)ethylbicyclo[2.2.1]-hept-2-yl]-5-heptenoic acid, methyl ester, the title C alcohol is obtained.

[1β,2α(Z),3α,4β]-7-[3-[4-[[[(1-Oxohexyl)amino]acetyl]amino]butyl]-bicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 47

[1β,2α(5Z),3α,4β]-8-[3-[[[[(1-Oxohexyl)amino]-acetyl]amino]methyl]bicyclo[2.2.1]hept-2-yl]-5-octenoic acid A. 1β,2α,3α,4β)-3-(Hydroxymethyl)-bicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) is chilled to 0° C. and treated dropwise with 1.4M potassium t-amylate in toluene (1910 ml, 2.67 mol) over 20 minutes. The resultant solution is stirred at 0° C. for 1 hour. The mixture is then treated slowly over 5 minutes with solid hemiacetal (XIII in reaction sequence C) prepared as described in U.S. Pat. No. 4,452,160 (1.28 mol). The mixture is stirred vigorously at room temperature for 90 minutes. The reaction mixture is then chilled to 0° C. and treated slowly with acetaldehyde (124 ml, 2.2 mol) over 10 minutes. The mixture is diluted with water (2500 ml) and treated with 10% hydrochloric acid to pH 7. The mixture is then extracted with ether (7×2 liters). The combined ether extracts are dried over magnesium sulfate, filtered, and the filtrates concentrated in vacuo. The resultant mixture is treated with isopropyl ether (4 liters) and stirred overnight. The mixture is chilled to −10° C. for 90 minutes then filtered. The solids are washed thoroughly with isopropyl ether. The filtrate is concentrated in vacuo to an oily residue. This oily residue is treated with water (4000 ml) and stirred vigorously for 2 hours. The aqueous layer is decanted and the oily residue treated two additional times with water (2×liter). After the third wash, the residue solidifies and is filtered. The combined aqueous triturates are concentrated in vacuo to 3.5 liters. The mixture is filtered through a bed of Celite. The filtrate is concentrated again to a volume of 2.3 liters. The cloudy solution is chilled in an ice bath and treated slowly with concentrated hydrochloric acid (683 ml). The mixture is then stirred at room temperature for 3 hours. After this time the solution is neutralized by the slow addition of solid sodium bicarbonate (720 g). The mixture is filtered through a bed of Celite then extracted with hexane (4×2 liters) then ethyl acetate (10×2 liters). The combined ethyl acetate extracts are dried over $MgSO_4$ and concentrated in vacuo to yield desired compound (hemiacetal F in reaction sequence C).

The above Wittig procedure is repeated on the hemiacetal F used in place of hemiacetal XIII to form the title aldehyde.

B.

[1β,2α(Z),3α,4β,]-8-3-(Hydroxy-methyl)bicyclo[2.2.1]hept-2-yl]-5-octenoic acid, methyl ester A Wittig reagent is prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds forms, an equivalent amount of base is added to form the ylide. To this deep orange solution is added a solution of Part A aldehyde (6 mmole) in 20 ml of dimethyl sulfoxide and the resulting mixture stirred at room temperature for 45 minutes. The reaction is quenched by addition of 24 mmole of acetic acid and the mixture poured into brine (300 ml) and extracted with ether (3×200 ml). Concentration of these extracts gives an oil which is stirred with saturated sodium bicarbonate solution until crystalline triphenylphosphine oxide forms in the mixture. This mixture is washed with benzene and acidified with 10% hydrochloric acid. The aqueous layer is saturated with salt and extracted with ether which on drying (sodium sulfate) and concentration gives crude product. The mixture is stirred 24 hours with 10% aqueous sodium hydroxide and reisolated by acidification and ether extraction. The product is purified by silica gel chromatography to give acid. This is treated with diazomethane (CH$_2$N$_2$) in Et$_2$O to give the title compound.

C. [1β,2α(Z),3α,4β]-8-[3-[[[[(1-Oxohexyl)-amino]acetyl-]amino]methyl]bicyclo-[2.2.1]hept-2-yl]-5-octenoic acid Following the procedure of Examples 1 and 2 except substituting the title B ester for the ester used in Example 1 Part B, the title compound is obtained.

EXAMPLE 48

[1β,2α(Z),3α,4β]-6-[3-[[[(1-Oxohexyl)amino]-acetyl-]amino]methyl]bicyclo[2.2.1]hept-2-yl]-1-(1H-tetrazol-5-yl)-4-hexene Example 9 Part A aldehyde (1.02 mmol) and triphenyl-4-(1H-tetrazol-5-yl)butyl phosphonium bromide (509 mg, 1.4 mmol) are suspended in distilled THF (20 ml) in an argon atmosphere. After cooling in an ice bath, 1.6M potassium t-amylate in toluene (2.1 ml, 3.4 mmol) is added dropwise and the mixture left stirring overnight at room temperature.

After quenching the Wittig reaction with acetic acid (0.7 mol), ethyl acetate (80 ml) is added. A solid is removed by filtration. The filtrate is taken to dryness in vacuo. A 5% solution of K$_2$CO$_3$ (50 ml) is added. A solid (which contained some starting aldehyde) is removed by filtration. The filtrate is washed with a toluene-ether (1:1) mixture (2×50 ml) and then acidified with concentrated HCl. Solid NaCl is added and the product is extracted into CHCl$_3$ (3×50 ml). The chloroform extracts are dried (MgSO$_4$), filtered and freed of solvent in vacuo leaving a yellow oil (390 mg). This is purified by chromatography on preparative reverse phase HPLC using a fully capped C$_{18}$ column (YMC-100A, ODS, 20×500 mm, 15μ spherical) with CH$_3$CN/H$_2$O, 42/58 (water contains 0.05% H$_3$PO$_4$), flow rate 25 ml/min, UV detector (200 mμ).

The CH$_3$CN is removed in vacuo. Solid NaCl is added to the aqueous residue. The product is extracted into chloroform (3×50 ml), washed with saturated NaCl solution (15 ml), dried (MgSO$_4$) and freed of solvent in vacuo to afford title compound.

EXAMPLE 49

[1β,2α(5Z),3α,4β]-7-[3-[[[(1-Oxohexyl)amino]-acetyl-]amino]methyl]bicyclo[2.2.1]hept-2-yl]-N-hydroxy-N-methyl-5-heptenamide A solution of Example 2 acid (0.82 mmole) in dry benzene (5.0 ml) is treated with oxalyl chloride (1 ml; 11.24 mmole or 13.7 eq.) and a drop of DMF, and stirred at room temperature under nitrogen for 2 hours. The excess oxalyl chloride and solvent are blown off by a stream of nitrogen while heating the reaction flask in a warm water bath and the oil obtained dried in vacuo (oil pump) for 1 hour. The residual acid chloride is dissolved in dry tetrahydrofuran (1.5 ml) and added dropwise into a cold solution (0°, ice-water) of 98% methylhydroxylamine hydrochloride (139.8 mg; 1.64 mmole; 2 eq.) and triethylamine (0.34 ml; 2.46 mmole; 3 eq.) in tetrahydrofuran (2 ml) and water (2.0 ml). The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 50

[1β,2α(6Z),3α,4β]-7-[3-[[[[(1-Oxohexyl)amino]-acetyl-]amino]methyl]bicyclo[2.2.1]hept-2-yl]-6-heptenoic acid

A.

[1β,2α(6Z),3α,4β]-7-[3-(Hydroxymethyl)bicyclo[2.2.1-]hept-2-yl]-heptenoic acid, methyl ester A slurry of carboxypentyl triphenylphosphonium bromide in THF is cooled in an ice bath and treated dropwise with 1.4 M KOt-amylate in toluene. After completion of this addition, the reaction mixture is allowed to warm to room temperature and is stirred for 6 hours. To this stirred solution is then added a solution of hemiacetal XIII (reaction sequence G) (prepared as described in Example 3 of U.S. Pat. No. 4,452,160) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated NaHCO$_3$ solution. The aqueous extracts are acidified to pH~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title ester.

B.

[1β,2α(6Z),3α,4β]-7-[3-[[[[(1-Oxohexyl)-amino]acetyl-]amino]methyl]bicyclo-[2.2.1]hept-2-yl]-6-heptenoic acid Following the procedure of Example 1 except substituting the Part A ester for the hydroxymethyl compound used in Example 1 Part B, the title compound is obtained.

EXAMPLE 51

[1β,2α(2E),3α,4β-7-[3-[[[[(1-Oxohexyl)amino]-acetyl-]amino]methyl]bicyclo[2.2.1]hept-2-yl]-2-heptenoic acid

A.

(1β,2α,3α,4Γ)-5-[3-(Hydroxymethyl)-bicyclo[2.2.1-]hept-2-yl]pentanal

Following the procedure of Example 47 Part A, except substituting (1β,2α,3α,4β)-3-[3-(hydroxymethyl)-bicyclo[2.2.1]hept-2-yl]-propionaldehyde for the hemiacetal XIII (see reaction sequence C or E), (1β,2α,-3α,4β)-4-[3-(hydroxymethyl)bicyclo[2.2.1]hept-2-yl]butanal is obtained. Then by repeating the procedure of Example 47 Part A on (1β,2α,3α,4β)-4-[3-(hydroxymethyl)bicyclo[2.2.1-hept-2-yl] butanal, the title A aldehyde is produced.

B.

[1β,2α(2E),3α,4β]-7-[3-(Hydroxymethyl)bicyclo[2.2.1-]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C.
[1β,2α(2E),3α,4β-7-[3-[[[[(1-Oxohexyl)amino]acetyl]amino]methyl]-bicyclo[2.2.1]hept-2-yl]-2-heptenoic acid Following the procedure of Example 1 except substituting the Part B ester for the ester used in Example 1 Part B, the title compound is obtained.

EXAMPLE 52

[1β,2α(5Z),3α,4β]6-7-[3-[(Methylamino)methyl]-bicyclo[2.2.1]hept-2-yl]-5-heptenoic acid, methyl ester Chiral amine from Example 1, Part C, (1 mmole) and N,N-dimethylformamide dimethylacetal (1.5 mmole) are dissolved in $CH_2Cl_2$ (6 ml). The reaction is stirred at room temperature overnight. The solvent and the excess reagent are evaporated to give crude amidine, which is dissolved in $CH_2Cl_2$ (5 ml). Methyl triflate (2 mmole) is added into the reaction at room temperature and the reaction is stirred for 1 hour at room temperature. The organic solvent and the excess reagent are evaporated off in vacuo and the residue is treated with methanolic hydrogen chloride at room temperature overnight. The reaction is concentrated in vacuo and the resulting crude product is dissolved in 1N HCl. The water layer is washed with ethyl ether and basified with saturated $NaHCO_3$. The water layer is extracted with ethyl ether, which is dried over $MgSO_4$. Filtration and evaporation of the solvent leave a crude product, which is purified by silica gel column to give the title compound.

The title compound is then employed in place of the chiral amine from Example 1 Part C to prepare compounds of the invention wherein $R_1$ is $CH_3$.

EXAMPLE 53

[1β,2α(5Z),3α,4β]-7-[3-[[[[(1-Oxononyl)amino]-acetyl]amino]methyl]bicyclo[2.2.1]hept-2-yl]-5-heptenoic acid, methyl ester A. N-Nonanoyl glycine Glycine (20 mmol) was reacted with nonanoyl chloride (22 ml) in the presence of NaOH (40 mmol) in a mixture of water and ether as described in Example 1 Part A. The crude crystalline product (4.25 g) was recrystallized from ethyl acetate (40–50 ml) to give the title compound (3.42 g, 79.5%), m.p. 106°–109° C.

B.
[1β,2α(5Z),3α,4β]-7-[3-[[[[(1-Oxononyl)-amino]acetyl]amino]methyl]bicyclo-[2.2.1]hept-2-yl]-5-heptenoic acid, methyl ester Part A compound (1 mmol) is reacted with carbonyldiimidazole (1 mmol) followed by Examle 1 Part C chiral amine as described in Example 1 Part D. The crude product is chromatographed on silica gel to give the title ester.

EXAMPLE 54

[1β,2α(5Z),3α,4β]-7-[3-[[[[(1-Oxononyl)amino]-acetyl]amino]methyl]bicyclo[2.2.1]hept-2-yl]-5-heptenoic acid The Example 53 methyl ester (6.5 mmol) is hydrolyzed with LiOH in a THF-$H_2O$ mixture as described in Example 2.

EXAMPLE 55

[1β,2α(5Z),3α,4β]-7-[3-[[[[(1-Oxooctyl)amino]-acetyl]amino]methyl]bicyclo[2.2.1]hept-2-yl]-5-heptenoic acid, methyl ester A. N-Octanoylglycine Glycine (20 mmol) was reacted with octanoyl chloride (22 mmol) in the presence of NaOH (40 mmol) in a mixture of water and ether using the method described in Example 1 Part A. The crude crystalline product (3.06 g, 76%) was recrystallized from EtOAc (15 ml) to give the title compound (1.11 g, 28%), m.p. 105–107° C.

B. [1β,
2α(5Z),3α,4β]-7-[3-[[[[(1-Oxooctyl)amino]acetyl]amino]methyl]bicyclo [2.2.1]hept-2-yl]-5-heptenoic acid, methyl ester Part A compound (1 mmol) is reacted with carbonyldiimidazole (1 mmol), followed by Example 1 Part C chiral amine (1 mmol) as described in Example 1 Part D. The crude product is chromatographed on silica gel to give title ester.

EXAMPLE 55A

[1β,2α(5Z),3α,4β]-7-[3-[[[[(1-Oxooctyl)amino]acetyl]amino]methyl]bicyclo[2.2.1]hept-2-yl]5heptenoic acid The Example 55 methyl ester (0.726 mmol) is hydrolyzed with LiOH in a THF-$H_2O$ mixture as described in Example 2.

EXAMPLE 56

1β, 2α(5Z),3α,
4β]-7-[3-[[[[(1-Oxo-4-phenyl)-butyl]amino]acetyl]amino]methyl]bicyclo -[2.2.1]hept-2-yl]-5-heptenoic acid A. 4-Phenylbutanoyl glycine ethyl ester 4-Phenylbutyric acid (2.46 g, 15 mmol) was dissolved in distilled THF (70 ml) in an argon atmosphere. After cooling in an ice bath, carbonyldiimidazole (CDI) (2.43 g, 1.5 mmol) was added and the mixture was stirred cold 1 hour and at room temperature 1 hour. The mixture was then cooled and glycine ethyl ester •HCl (2.09 g, 15 mmol) and distilled $Et_3N$ (2.1 ml, 15 mmol) were added. The mixture was left stirring overnight at room temperature. After removal of the solvent in vacuo, $Et_2O$ (200 ml) was added. The solution was washed with 1N HCl (70 ml), 0.5 N NaOH (70 ml) and saturated NaCl solution (70 ml), dried ($MgSO_4$) and freed of solvent in vacuo leaving title compound (3.13 g, 84%) as white crystalline material. TLC: silica gel, $Et_2O$, UV; Rf: 0.58.

B. 4-Phenylbutanoyl glycine

The Part A ester (3.07 g, 12.3 mmol) was hydrolyzed with NaOH (5 g, 125 mmol) in water (60 ml). After stirring at room temperature 6 hours, neutral material was removed by washing with $Et_2O$ (2×50 ml). The aqueous solution was then acidified with concentrated HCl solution. The product was extracted into $CHCl_3$ ($3\times60$ ml), dried ($MgSO_4$) and freed of solvent in vacuo leaving a white solid. This was recrystallized from EtOAc (10 ml) to give title compound (2.18 g, 80%), m.p. 99–101° C.

C. [1β, 2α(5Z),3α,4β]-7-[3-[[[[(1-Oxo-4-phenyl)butyl-]amino]acetyl]amino]-methyl]bicyclo[2.2.1]hept-2-yl]-5-heptenoic acid, methyl ester Part B acid (1 mmol) is reacted with CDI (1 mmol) and then with Example 1 Part C chiral amine (1 mmol) as described in Example 5 Part B. The crude product is chromatographed on silica gel to give title compound.

D. [1β, 2α(5Z),3α,4β]-7-[3-[[[[(1Oxo-4-phenyl)butyl-]amino]acetyl]amino]methyl]bicyclo[2.2.1]hept-2-yl]-5-heptenoic acid The Part C methyl ester (0.71 mmol) is hydrolyzed with LiOH in a water-THF mixture as described in Example 6.

EXAMPLE 57

1α, 2β(Z),3β,4α]-7-[3-[[[[[(Phenylthio)acetyl]amino]acetyl-]amino]methyl]bicyclo[2.2.1]hept-2-yl]-5-heptenoic acid A. (Phenylthio)acetyl glycine ethyl ester The title ethyl ester was prepared from thiophenoxy acetic acid (15 mmol) and the ethyl ester of glycine•HCl using carbonyldiimidazole (CDI) as described in Example 56, Part A giving 2.95 g (78%) of solid.

B. (Phenylthio)acetyl glycine

The Part A ethyl ester was hydrolyzed with aqueous NaOH as described in Example 56 Part B to give the title acid (1.041 g, 92%) as a crystalline material.

C. [1α,2β(Z),3β,4α]-7-[3-[[[[[(Phenylthio)acetyl-]amino]acetyl]amino]methyl]bicyclo[2.2.1]hept-2-yl-5-heptenoic acid, methyl ester The Part B acid (1.5 mmol) is reacted with CDI (1.5 mmol) followed by Example 1 Part C chiral amine (1.5 mmol) as described in Example 5 Part B. The crude product is chromatographed on silica gel.

D. [1α,2β(Z),3β,4α]-7-[3-[[[[[(Phenylthio)acetyl-]amino]acetyl]amino]methyl]bicyclo[2.2.1]hept-2-yl]-5-heptenoic acid The Part C methyl ester (0.98 mmol) is hydrolyzed with 1N LiOH (2 equivalents) as described in Example 6.

EXAMPLE 58

[1α, 2β(Z),3β,4α]-7-[3-[[[[3-(4-Hydroxyphenyl)-1-oxo-propyl]amino]acetyl]amino]methyl]bicyclo[2.2.1]hept-2-yl]-5-heptenoic acid A. 3-(4-Hydroxyphenyl)propanoyl glycine ethyl ester 3-(4-Hydroxyphenyl)propionic acid (2.49 g, 15 mmol) was reacted with glycine ethyl ester hydrochloride in the presence of CDI and $Et_3N$ as described in Example 56 Part A. After removal of the solvent the residue was dissolved in $CHCl_3$ and washed with 1N HCl, saturated $NaHCO_3$ solution and saturated NaCl solution. After drying ($MgSO_4$) and removal of the solvent in vacuo crude title ester remained (2.44 g) as a viscous oil. NMR indicated this contained a major impurity but it was used without further purification.

B. 3-(4-Hydroxyphenyl)propanoyl glycine

Crude Part A ethyl ester was hydrolyzed with NaOH in water as described in Example 56 Part B to give a white solid (1.37 g). This was recrystallized from EtOAc•MeOH to give the title solid (0.98 g, 29% from starting acid).

C. [1α,2β(Z),3β,4α]-7-[3-[[[[3-(4-Hydroxyphenyl)-1-oxo-propyl]amino]acetyl]amino]methyl]bicyclo[2.2.1]hept-2-yl]-5-heptenoic acid, methyl ester Example 1, Part C chiral amine (1.5 mmol) is dissolved in distilled THF (20 ml) in an argon atmosphere. Part B acid (346 mg, 1.55 mmol) is added and the mixture is cooled in an ice bath. Dicyclohexylcarbodiimide (DCC) (319 mg, 1.55 mmol) is added and the mixture is stirred cold 20 minutes and at room temperature overnight. 1N HCl (4 drops) is added and after stirring 10 minutes the solvent is removed in vacuo. EtOAc (8 ml) is added to the residue. After cooling in an ice bath the solid is removed by filtration and washed with cold EtOAc (~10 ml). The filtrate is freed of solvent in vacuo and the remaining material is chromatographed on silica gel to give title ester.

D. [1α,2β(Z),3β,4α]-7-[3-[[[[3-(4-Hydroxyphenyl)-1-oxo-propyl]amino]acetyl]amino]methyl]bicyclo[2.2.1]hept-2-yl]-5-heptenoic acid The Part C methyl ester (0.51 mmol) is dissolved in distilled THF (20 ml) and water (2 ml) in an argon atmosphere and treated with 1N LiOH solution (3 ml). The reaction is complete in 1 hour and at 2 hours is worked up as described in Example 6 to form the title product.

EXAMPLE 59

[1α,2β(Z),3β,4α]-7-[3-[[[[(Phenoxyacetyl-)amino]acetyl]amino]methyl]bicyclo[2.2.1]hept-2-yl]-5-heptenoic acid A. Phenoxyacetyl glycine Glycine (20 mmol) was reacted with distilled phenoxyacetyl chloride (22 mmol) in the presence of NaOH (40 mmol) in a mixture of water and ether as described in Example 5 Part A. The crude product was recrystallized from EtOAc (15 ml) to give title acid (2.38 gm, 57%).

B. [1α,2β(Z),3β,4α]-7-[3-[[[[(Phenoxyacetyl-)amino]acetyl]amino]methyl]bicyclo[2.2.1]hept-2-yl]-5-heptenoic acid, methyl ester Part A acid (1.5 mmol) is reacted with CDI (1.5 mmol), followed by Example 1 Part C chiral amine (1.5 mmol) as described in Example 5, Part B. The crude product is chromatographed on silica gel to give title ester.

C.

[1α,2β(Z),3β,4α]-7-[3-[[[[(Phenoxyacetyl-)amino]acetyl]amino]methyl]bicyclo[2.2.1]hept-2-yl]-5-heptenoic acid The Part B methyl ester (1.01 mmol) is hydrolyzed with 1N LiOH (2 equivalents) in a THF-$H_2O$ mixture as described in Example 6 to give the title acid.

EXAMPLE 60

[1α,2β(5Z),3β,4α]-7-[3-[[[[(1-Oxo-3-phenylpropyl-)amino]acetyl]amino]methyl]bicyclo[2.2.1]hept-2-yl]-5-heptenoic acid A. 3-Phenylpropanoyl glycine Glycine (1.5 g, 20 mmol) and hydrocinnamoyl chloride (3.37 g, 22 mmol) were reacted in the presence of NaOH (40 mmol) in a mixture of water and ether using the method described in Example 5 Part A. The crude product was extracted into chloroform, dried ($MgSO_4$) and freed of solvent in vacuo leaving a near white solid (3.53 g, 85%) This was recrystallized from EtOAc (13 ml) to give title compound (2.66 g, 64%) m.p. 112–114° C.

B.

[1α,2β(5Z),3β,4α]-7-[3-[[[[(1-Oxo-3-phenylpropyl-)amino]acetyl]amino]methyl]bioyclo[2.2.1]hept-2-yl]-5-heptenoic acid, methyl ester Part A acid (1 mmol) is reacted with CDI (1 mmol) and then with Example 1 Part C chiral amine (1 mmol) as described in Example 5 Part B.

The crude product is chromatographed on silica gel to give title compound.

C.

[1α,2β(5Z),3β,4α]-7-[3-[[[[(1-Oxo-3-phenylpropyl-)amino]acetyl]amino]methyl]bicyclo[2.2.1]hept-2-yl]-5-heptenoic acid The Part B methyl ester (0.72 mmol) is hydrolyzed with LiOH in a water-THF mixture as described in Example 6. The crude crystalline product is recrystallized to give title compound.

EXAMPLE 61

[1α,2β(5Z),3β,4α]-7-[3-[[[[(1-Oxo-5-phenylpentyl-)amino]acetyl]amino]methyl]bicyclo[2.2.1]hept-2-yl]-5-heptenoic acid A. 5-Phenylpentanoyl glycine ethYl ester 5-Phenylvaleric acid (2.67 g, 15 mmol) in distilled THF was reacted with CDI (15 mmol) followed by glycine ethyl ester•HCl (15 mmol) and $(C_2H_5)_3N$ (15 mmol) as described in Example 56 Part A. The crude material (3.25 g, 82%) was used without purification.

B. 5-Phenylpentanoyl glycine

The Part A ester (12.34 mmol) was hydrolyzed with NaOH in water as described in Example 56 Part B. The crude product was recrystallized from EtOAc (12 ml) to give title compound (2.39 g, 82%), m.p. 93–96° C.

C.

[1α,2β(5Z),3β,4α]-7-[3-[[[[(1-Oxo-5-phenylpentyl-)amino]acetyl]amino]methyl]bicyclo[2.2.1]hept-2-yl]-5-heptenoic acid, methyl ester Part B compound (1 mmol) is reacted with CDI (1 mmol) and then with Example 1 Part C chiral amine (1 mmol) as described in Example 5 Part B. The crude product is chromatographed on silica gel to give title compound.

D.

[1α,2β(5Z),3β,4α]-7-[3-[[[[(1-Oxa-5-phenylpentyl-)amino]acetyl]amino]methyl]bicyclo[2.2.1]hept-2-yl]-5-heptenoic acid The Part C methyl ester (0.749 mmol) is hydrolyzed with LiOH in a water-THF mixture as described in Example 6.

EXAMPLE 62

[1α,2β(Z),3β,4α]-7-[3-[[[[(4-Cyclohexyl-1-oxobutyl-)amino]acetyl]amino]methyl]bicyclo[2.2.1]hept-2-yl]-5-heptenoic acid A. 4-Cyclohexylbutanoic acid 4-Phenylbutanoic acid prepared as described in Example 56, Part A was dissolved in glacial acetic acid (25 ml). Platinum oxide (0.1 g) was added and the solution was hydrogenated in the Paar shaker at up to 55 p.s.i. until hydrogen uptake ceased (6.5 hours). The catalyst was removed by filtration and the acetic acid was removed in vacuo. The product crystallized and was recrystallized from $Et_20$ (20 ml) to give title compound (1.18 g, 77%), m.p. 85–88° C.

B.

[1α,2β(Z),3β,4α]-7-[3-[[[[(4-Cyclohexyl-1-oxobutyl-)amino]acetyl]amino]methyl]bicyclo[2.2.1]hept-2-yl]-5-heptenoic acid, methyl ester The Part A acid (341 mg, 1.5 mmol) is dissolved in $CHCl_3$ (10 ml) in an argon atmosphere. The solution is cooled in an ice bath and carbonyldiimidazole (2.43 mg, 1.5 mmol) is added. The mixture is stirred cold 30 minutes and at room temperature 1 hour. The hydrochloride of the chiral amine (prepared as described in Example 1 Part C) (1.5 mmol) is added. The solution is cooled in an ice bath and tri-n-butylamine (0.36 ml, 278 mg, 1.5 mmol) is added and the mixture is left stirring overnight at room temperature. More $CHCl_3$ (40 ml) is added and the solution is washed with 1N HCl (20 ml), saturated $NaHCO_3$ solution (20 ml) and saturated NaCl solution (20 ml). After drying ($MgSO_4$), the solvent is removed in vacuo. The product is purified by chromatography on silica gel to give the title methyl ester.

C.

[1α,2β(Z),3β,4α]-7-[3-[[[[(4-Cyclohexyl-1-oxobutyl-)amino]acetyl]amino]methyl]bicyclo[2.2.1]hept-2-yl]-5-heptenoic acid The Part B methyl ester (1.39 mmol) is hydrolyzed with LiOH as described in Example 6.

EXAMPLE 63

[1α,2β(Z),3β,4α]-7-[3-[[[[[1-Oxo-3-(phenylthio)propyl-]amino]acetyl]amino]methyl]bicyclo[2.2.1]hept-2-yl]-5-heptenoic acid A. 3-(Phenylthio)propanoic acid, methyl ester Thiophenol (440 mg, 4 mmol) and $Et_3N$ (70 μl, 0.5 mmol) were dissolved in $CH_2Cl_2$ (5 ml). Methyl acrylate (412 mg, 4.8 mmol) was added dropwise. The reaction was exothermic. After stirring at room temperature for 30 minutes, the excess methyl acrylate was removed in vacuo. TLC: silica gel, $Et_2O$-hexane 1:2, UV $R_f$=0.58. The crude title ester was used without further purification.

B. 3-(Phenylthio)propanoic acid

The crude Part A methyl ester (~4 mmole) was treated with 10 ml 1N NaOH and THF (5 ml). After stirring at room temperature 3 hours, ether (30 ml) was added. The layers were separated and the ether layer was reextracted with 1N NaOH solution (10 ml). The combined aqueous layers were washed with $Et_2O$ (20 ml) and then acidified with concentrated HCl. The product was extracted with $CHCl_3$ (2×30 ml). The chloroform extracts were washed with saturated NaCl solution (2×20 ml), dried ($MgSO_4$) and freed of solvent in vacuo leaving title acid as a white solid (quant.). This was used without further purification.

C. 3-(Phenylthio)propanoyl glycine ethyl ester

Part B acid (0.740 g, 4.06 mmol) was reacted with carbonyldiimidazole (4.06 mmol) followed by glycine ethyl ester•HCl (4.06 mmol) as described in Example 56 Part A to give the title ester (1.00 g, 92%) as crystalline material.

D. 3-(Phenylthio)propanoyl glycine

The Part C ethyl ester (0.96 g, 3.6 mmol) was hydrolyzed with NaOH solution as described in Example 56 Part B to give a white solid which was triturated with $Et_2O$ to give title acid (0.75 g, 87%).

E.

[1α,2β(Z),3β,4α]-7-[3-[[[[1-Oxo-3-(phenylthio)propyl]amino]acetyl]methyl]bicyclo[2.2.1]hept-2-yl]-5-heptenoic acid, methyl ester The Part D acid (359 mg, 1.5 mmol) is reacted with carbonyldiimidazole (1.5 mmol) followed by the hydrochloride of Example 1 Part C chiral amine by the procedure described in Example 62 Part B. The crude product is chromatographed on silica gel to give the title methyl ester.

F.

[1α,2β(Z),3β,4α]-7-[3-[[[[1-Oxo-3-(phenylthio)propyl]amino]acetyl]amino]-methyl]bicyclo[2.2.1]hept-2-yl]-5-heptenoic acid The Part E methyl ester (1.285 mmol) is dissolved in THF (25 ml) and $H_2O$ (2.5 ml) in an argon atmosphere and treated with 1N LiOH solution (2.6 ml). The mixture is stirred at room temperature for 5 hours and then worked up as described in Example 6. The crude product is chromatographed on silica gel to give title acid.

EXAMPLE 64

[1α,2β(Z),3β,4α]-7-[3-[[[[[(Phenylmethyl)thio]acetyl]amino]acetyl]amino]methy]bicyclo[2.2.1]hept-2-yl]-5-heptenoic acid A. Chloroacetyl glycine Glycine (1.5 g, 20 mmol) was dissolved in 2N NaOH (25 ml, 50 mmol) and ether (20 ml) was added. Chloroacetyl chloride (2.26 g) dissolved in $Et_2O$ (20 ml) was added dropwise at 0° C. The mixture was stirred at 0° for 30 minutes and at room temperature 1 hour. The layers were separated and the water layer was washed with $Et_2O$ (2×20 ml). The water layer was then acidified to pH 2 with concentrated HCl and the product was extracted into EtOAc (3×50 ml). The combined EtOAc extracts were washed with brine, dried ($MgSO_4$), and freed of solvent in vacuo to give title acid compound as a solid (2.56 g, 84%) which was used without further purification.

B. (Benzylthio)acetyl glycine

Part A acid (1.28 g, 8.4 mmol) was dissolved in methanol (10 ml) and cooled in an ice bath. Sodium methoxide (1.08 g, 20 mmol) was added followed by dropwise addition of benzyl mercaptan (1.25 g, 10.08 mmoles). After stirring overnight at room temperature, 1N NaOH solution (10 ml) was added. Ether washes (2×40 ml) removed neutral material. The aqueous layer was then acidified to pH 2 with concentrated HCl. The product was extracted with $Et_2O$ (3×50 ml), washed with brine, dried ($MgSO_4$) and freed of solvent in vacuo leaving a white solid. This was recrystallized from benzene to give title acid compound (1.28 g, 64%).

C.

[1α,2β(Z),3β,4α]-7-[3-[[[[[(Phenylmethyl)thio]acetyl]amino]acetyl]amino]methyl]bicyclo[2.2.1]hept-2-yl]-5-heptenoic acid, methyl ester Part B acid (1.5 mmol) is reacted with carbonyldiimidazole (1.5 mmol) followed by Example 1 Part C chiral amine•HCl 3 (1.5 mmol) using the procedure described in Example 62. The crude product is chromatographed on silica gel to give title ester.

D.

[1α,2β(Z),3β,4α]-7-[3-[[[[[(Phenylmethyl)thio]acetyl]amino]acetyl]amino]methyl]bicyclo[2.2.1]hept-2-yl]-5-heptenoic acid The Part C methyl ester (1.28 mmol) is hydrolyzed with 1N LiOH solution (2.6 ml) in a THF-water mixture as described in Example 6.

EXAMPLE 65

[1α,2β(Z),3β,4α]-7-[3-[[[[(Butylthio)acetyl]amino]acetyl]amino]methyl]bicyclo[2.2.1]hept-2-yl]-5-heptenoic acid A. (Butanethio)acetyl glycine Example 64 Part A acid compound (1.28 g, 8.4 mmol) was reacted with 1-butanethiol using the procedure described in Example 64. The crude product was crystallized with diisopropylether (~10 ml) to give title acid (0.55 g, 32%).

B.

[1α,2β(Z),3β,4α]-7-[3-[[[[(Butylthio)acetyl]amino]acetyl]amino]methyl]bicyclo[2.2.1]hept-2-yl]-5-heptenoic acid, methyl ester Part A acid (1.5 mmol) is reacted with carbonyldiimidazole (1.5 mmol) followed by Example 1 Part C chiral amine hydrochloride (1.5 mmol) using the procedure described in Example 62. The crude product is chromatographed on silica gel to give title compound.

C.

[1α,2β(Z),3β,4α]-7-[3-[[[[(Butylthio)acetyl]amino]acetyl]amino]methyl]bicyclo[2.2.1]hept-2-yl]-5-heptenoic acid The Part B methyl ester (1.18 mmol) is hydrolyzed with 1N LiOH solution (2.4 ml) in a tetrahydrofuran-water mixture using the procedure described in Example 6.

EXAMPLE 66

[1α,2β(Z),3β,4α]-7-[3-[[[[[(Cyclohexylmethyl)thio]acetyl]amino]acetyl]amino]methyl]bicyclo[2.2.1]hept-2-yl]-5-heptenoic acid A. Cyclohexylmethylthiol acetate Cyclohexylmethyl mesylate (1.92 g, 10 mol) and $KSCOCH_3$ (1.25 g) were suspended in distilled tetrahydrofuran (THF). The reaction mixture was heated under reflux for 3 hours. Additional $KSCOCH_3$ (1.25 g) and THF (9 ml) were added and the mixture was heated under reflux an additional 3 hours. $Et_2O$ (100 ml) was added and the mixture was washed with brine (30 ml). The aqueous layer was reextracted with $Et_2O$ (30 ml). The combined organic layers were washed with brine (15 ml), dried ($MgSO_4$) and freed of solvent to give a straw colored oil (1.8 g). This was chromatographed on silica gel (50 g, Baker for flash chromatography) eluting with 2% $Et_2O$ in hexane to give title compound (1.189 g, 69%) as an oil. TLC: silica gel, 10% $Et_2O$ in hexane, UV and $I_2$, Rf=0.48.

B. [(Cyclohexylmethyl)thio]acetyl glycine

Part A compound (6 mmol) and the Example 64 Part A acid (6 mmol) were reacted in the presence of NaOMe (17 mmol) as described in Example 64 Part B. The crude product was crystallized from diisopropyl ether to give title compound (516 mg, 35%).

C.

[1α,2β(Z),3β,4α]-7-[3-[[[[[(Cyclohexylmethyl)thio]acetyl]amino]acetyl]amino]methyl]bicyclo[2.2.1]hept-2-yl]-5-heptenoic acid, methyl ester Part B compound (1.5 mmol) is coupled with Example 1 Part C chiral amine•HCl (1.5 mmol) in the presence of carbonyl diimidazole (CDI) (1.5 mmol) as described in Example 62 Part B. The crude product is chromatographed on silica gel to give title compound.

D.

[1α,2β(Z),3β,4α]-7-[3-[[[[[(Cyclohexylmethyl)thio]acetyl]amino]acetyl]amino]methyl]bicyclo[2.2.1]hept-2-yl]-5-heptenoic acid The Part C methyl ester (1.09 mmol) is hydrolyzed with 1N LiOH (4 ml) in a mixture of THF and water as described in Example 6.

EXAMPLE 67

[1α,2β(Z),3β,4α]-7-[3-[[[[(Phenylsulfinyl)acetyl]amino]acetyl]amino]methyl]bicyclo[2.2.1]hept-2-yl]-5-heptenoic acid Powdered $NaIO_4$ (385 mg, 1.8 mmol) is dissolved in water (12 ml). A solution of Example 57 acid compound (0.6 mmol) in methanol (20 ml) is added. The mixture is stirred overnight at room temperature. Most of the methanol is removed in vacuo. Saturated NaCl solution (50 ml) is added. The product is extracted with $CHCl_3$ (3×50 ml). The combined chloroform extracts are washed with NaCl solution (20 ml), dried ($MgSO_4$), and freed of solvent in vacuo leaving an oil. This is chromatographed on silica gel to give title acid.

EXAMPLE 68

[1α,2β(Z),3β,4α]-7-[3-[[[[(Phenylsulfonyl)acetyl]amino]acetyl]amino]methyl]bicyclo[2.2.1]hept-2-yl-5-heptenoic acid Example 67 acid compound (0.9 mmol) is dissolved in methanol (10 ml) and cooled in an ice bath. Oxone (810 mg ~2.7 mmol) dissolved in water (10 ml) is added. The mixture is stirred at room temperature 4 hours, then diluted with water (30 ml). The product is extracted into $CHCl_3$ (35×35 ml). The combined $CHCl_3$ extracts are washed with saturated NaCl solution (2×20 ml), dried ($MgSO_4$), and freed of solvent in vacuo leaving an oil. This is chromatographed on silica gel to give title acid.

EXAMPLES 69 to 104

Following the procedures outlined in the specification and described in the above working Examples, the following compounds may be prepared.

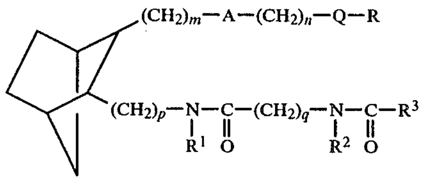

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 69. | 2 | CH=CH | $-CH(CH_3)-$ | CH=CH | $C(=O)N(H)-OCH_3$ | 3 | $C_2H_5$ | $(CH_2)_7$ | $C_3H_7$ | $-CH_2-C(H)=C(H)-CH_3-$ |
| 70. | 3 | $(CH_2)_2$ | $-C(CH_3)(CH_3)-$ | $CH_2$ | $C(=O)N(CH_3)-OC_2H_5$ | 4 | H | $-CH(CH_3)-$ | $C_4H_9$ | $OC_6H_5$ |
| 71. | 4 | $(CH_2)_2$ | $(CH_2)_4$ | $CH_2$ | $C(=O)NHC_6H_5$ | 1 | $C_3H_7$ | $-CH_2-$ | $C_5H_{11}$ | $C_6H_5$ |
| 72. | 1 | CH=CH | $-C(CH_3)(CH_3)-CH_2-$ | $-CH(F)-$ | $CO_2Li$ | 2 | H | $-CH_2-CH(CH_3)-$ | H | $CH_2C_6H_5$ |
| 73. | 0 | CH=CH | $-CH(CH_3)-CH(CH_3)$ | $-C(F)(F)-$ | $CO_2Na$ | 3 | $CH_3$ | $-CH_2-C(CH_3)(CH_3)-$ | H | $-(CH_2)_2C_6H_5$ |
| 74. | 1 | $(CH_2)_2$ | $-C(CH_3)(F)-CH_2-$ | CH=CH | $CO_2$ glucamine salt | 4 | $C_2H_5$ | $-CH_2-CH(CH_3)-CH_2-$ | H | $-C_6H_4-p-CH_3$ |
| 75. | 2 | CH=CH | $-CH(F)-CH(F)-$ | $CH_2$ | $CO_2$ tris salt | 1 | H | $-(CH_2)_3-$ | $CH_3$ | $-C_6H_4-p-OH$ |
| 76. | 3 | $(CH_2)_2$ | $-C(F)(F)-CH_2-$ | $CH_2$ | $CH_2OH$ | 2 | $C_4H_9$ | $-CH_2-CH(C_2H_5)-$ | $CH_3$ | $-OCH_2C_6H_5$ |

-continued

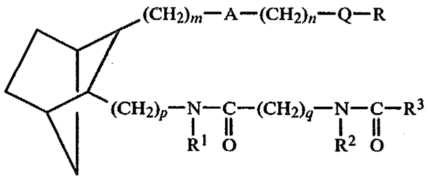

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 77. | 4 | $(CH_2)_2$ | $-(CH_2)_5$ | $-CH(F)-$ | 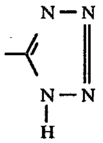 | 3 | H | $-CH_2-C(CH_3)(H)-CH_2-$ | $CH_3$ | $-SC_2H_5$ |
| 78 | 0 | CH=CH | $-CH_2-CH(CH_3)-CH_2-$ | $-CF_2-$ | $C(=O)NH_2$ | 4 | $CH_2$ | $-C(CH_3)_2-CH_2-$ | $C_2H_5$ | $-OC_6H_5$ |
| 79. | 0 | $(CH_2)_2$ | $-CH_2-C(CH_3)_2-$ | — | $C(=O)N(H)OH$ | 1 | $C_2H_5$ | $(CH_2)_2$ | $CH_3$ | $-NH_2$ |
| 80. | 1 | CH=CH | $CH_2$ | — | $C(=O)N(CH_3)_2$ | 2 | $C_2H_5$ | $-CH_2-$ | H | $-NHCH_3$ |
| 81. | 2 | $(CH_2)_2$ | $(CH_2)_2$ | $CH_2$ | $C(=O)N(OH)-CH_3$ | 3 | $CH_3$ | $-CH_2-C(CH_3)_2-$ | $C_4H_9$ | $-NHC_6H_5$ |
| 82. | 3 | CH=CH | $(CH_2)_3$ | — | $CO_2H$ | 4 | $C_2H_5$ | $-CH_2-CH(CH_3)-CH(CH_3)-CH_2-$ | $CH_3$ | $NCH_3(C_2H_5)$ |
| 83. | 4 | $(CH_2)_2$ | $(CH_2)_4$ | CH=CH | $CH_2OH$ | 1 | $C_3H_7$ | $(CH_2)_2$ | $C_2H_5$ | $-N(CH_3)_2$ |
| 84. | 0 | CH=CH | $-(CH_2)_3-$ | — | 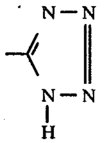 | 1 | $C_6H_{13}$ | $CH_2$ | H | H |

-continued

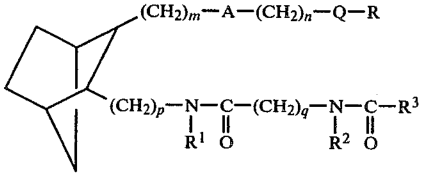

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 85. | 1 | $(CH_2)_2$ | 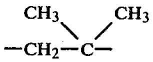 | $CH_2$ | 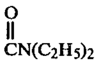 | 3 | $C_5H_{11}$ | 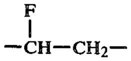 | $C_3H_7$ | $-NH-CH_2-C_6H_5$ |
| 86. | 2 | $CH{=}CH$ | $(CH_2)_5$ | 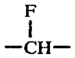 | 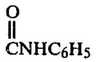 | 4 | H | 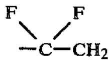 | $CH_4H_9$ | $-(CH_2)_2CH{=}CHCH_3$ |
| 87. | 3 | $(CH_2)_2$ | 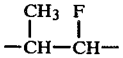 | 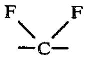 | $CH_2OH$ | 1 | H | $(CH_2)_2$ | H | $C_6H_5$ |
| 88. | 4 | $(CH_2)_2$ | $(CH_2)_2$ | $CH{=}CH$ | 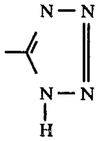 | 2 | H | $CH_2$ | H | $-CH_2C_6H_5$ |
| 89. | 0 | $CH{=}CH$ | $(CH_2)_3$ | $CH_2$ | $CO_2CH_3$ | 3 | $CH_3$ | $(CH_2)_3$ | $C_3H_7$ | $-SC_4H_9$ |
| 90. | 2 | $(CH_2)_2$ | $(CH_2)_4$ | $CH_2$ | $CO_2CH_3$ | 4 | $CH_3$ | $(CH_2)_8$ | H | $-SC_6H_5$ |
| 91. | 3 | $CH{=}CH$ | $(CH_2)_5$ | — | $CO_2H$ | 1 | $CH_3$ | $(CH_2)_{10}$ | H | $-NCH_3(C_6H_5)$ |
| 92. | 2 | $CH{=}CH$ | $CH_2$ | $CH{=}CH$ | $CO_2H$ | 1 | H | $(CH_2)_2$ | $CH_3$ | H |
| 93. | 3 | $(CH_2)_2$ | $(CH_2)_2$ | $CH_2$ | $CH_2OH$ | 2 | $C_2H_5$ | $(CH_2)_3$ | H | $CH_3$ |
| 94. | 4 | $CH{=}CH$ | $(CH_2)_3$ | $CH_2$ | 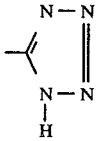 | 3 | H | $(CH_2)_4$ | H | $-CH{=}CH-CH_3$ |
| 95. | 1 | $(CH_2)_2$ | $(CH_2)_4$ | 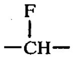 | 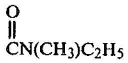 | 1 | $CH_3$ | $(CH_2)_5$ | $CH_3$ | $-C{\equiv}C-CH_3$ |

-continued

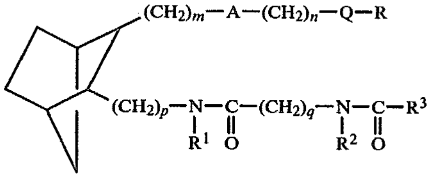

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 96. | 0 | CH=CH | $(CH_2)_5$ | 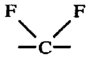 | 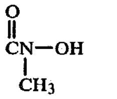 | 2 | H | $(CH_2)_6$ | $C_2H_5$ | $-CH_2-C\equiv C-CH_3$ |
| 97. | 1 | CH=CH | $(CH_2)_3$ | — | $CO_2H$ | 1 | H | $CH_2$ | H | $SC_6H_5$ |
| 98. | 1 | CH=CH | $CH_2$ | — | $CO_2H$ | 1 | H | $CH_2$ | H | 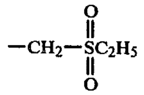 |
| 99. | 2 | $(CH_2)_2$ | $(CH_2)_3$ | $CH_2$ | $CH_2OH$ | 2 | $CH_3$ | $(CH_2)_2$ | H | $-CH_2-SCH_2C_6H_5$ |
| 100. | 3 | CH=CH | $(CH_2)_3$ | CH=CH | $CO_2H$ | 3 | H | $(CH_2)_3$ | H | $-CH_2-S-C_2H_5$ |
| 101. | 4 | $(CH_2)_2$ | $(CH_2)_3$ | — | 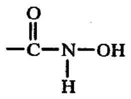 | 1 | $CH_5$ | $CH_2$ | $CH_3$ | $-CH_2-S-CH_2-C_6H_5$ |
| 102. | 2 | CH=CH | $(CH_2)_3$ | $CH_2$ | $CO_2H$ | 2 | H | $CH_2$ | H | $-CH_2-O-CH_2-C_6H_5$ |
| 103. | 3 | CH=CH | $CH_2$ | — | $CO_2H$ | 1 | $CH_3$ | $CH_2$ | H | 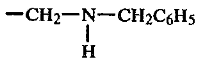 |
| 104. | 2 | $(CH_2)_2$ | $(CH_2)_3$ | $CH_2$ | $CO_2CH_3$ | 1 | H | $(CH_2)_2$ | $CH_3$ | $-CH_2-S-C_4H_9$ |

What is claimed is:

1. A compound having the structure

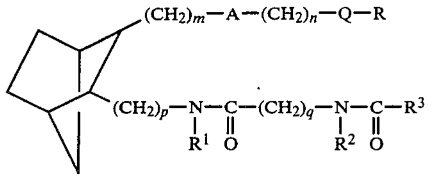

including all stereoisomers thereof, wherein m is 0 to 4; A is $-CH=CH-$ or $-CH_2-CH_2-$; n is 1 to 5; Q is $-CH=CH-$, $-CH_2-$,

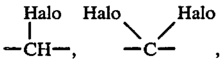

or a single bond; R is $C_2H$, $C_2$alkyl, $C_2$ alkali metal, $CO_2$ polyhydroxyamine salt, $-CH_2OH$,

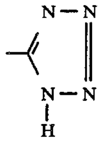

, or

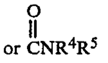

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; $R^2$ is H or lower alkyl; and $r^3$ is H, lower alkyl, lower alkenyl, lower alkynyl, aryl, arylalkyl, lower alkoxy, arylalkloxy, aryloxy, amino, alkylamino, arylamino, arylalkylamino, lower alkyl-s-, aryl-S-, arylalkyl-S-,

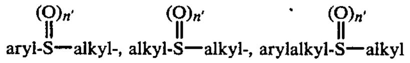

(wherein n' is 0, 1 or 2), alkylaminoalkyl, arylaminoalkyl, arylalkylaminoalkyl, alkoxyalkyl, aryloxyalkyl or arylalkoxyalkyl, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

cycloalkyl alone or as part of another group is a saturated cyclic hydrocarbon group containing 3 to 12 carbons, which is unsubstituted or substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonyl amino groups, 1 or 2 amino groups, 1 or 2 nitro groups, 1 or 2 cyano groups, 1 or 2 thiol groups and/or 1 or 2 alkylthio groups; and aryl alone or as part of another group refers to monocyclic or bicyclic aromatic groups containing from 6 to 10 carbons in the ring portion and which is unsubstituted or is substituted with 1 or 2 lower alkyl groups, 1 or 2 halogens, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro group, 1 or 2 cyano groups, 1 or 2 thiol groups and/or 1 or 2 alkylthio groups.

2. The compound as defined in claim 1 wherein $R^3$ is alkyl, alkoxy or arylthioalkyl.

3. The compound as defined in claim 1 wherein A is CH=CH.

4. The compound as defined in claim 1 wherein m is 1 and n is 1 to 4.

5. The compound as defined in claim 1 wherein p is 1 and q is 1.

6. The compound as defined in claim 1 wherein Q is a single bond or $CH_2$.

7. The compound as defined in claim 1 wherein R is $CO_2$ alkyl or $CO_2H$.

8. The compound as defined in claim 1 wherein $R^1$ is H and $R^2$ is H or $CH_3$.

9. The compound as defined in claim 1 wherein m is 1, n is 2 to 4, Q is $CH_2$, a single bond, CH=CH,

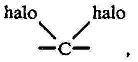

R is $CO_2$alkyl, $CO_2H$, $CH_2OH$, or

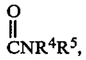

p is 1 $R^1$ is H, q is 1, $R^2$ is H or alkyl and $R^3$ is alkyl, alkoxy or phenylthiomethyl.

10. The compound as defined in claim 1 having the name [1β, 2α(5Z),3α,4β]7-[3-[[[[(1-oxohexyl-)amino]acetyl]amino]methyl]bicyclo[2.2.1hept-2-yl]-5-heptenoic acid or esters thereof, including all stereoisomers thereof.

11. A method of inhibiting platelet aggregation and/or bronchoconstriction, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A composition for inhibiting platelet aggregation and/or bronchoconstriction comprising an effective amount of a compound as defined in claim 1 or a pharmaceutically acceptable salt thereof, and a pharmaceutically acceptable carrier therefor.

14. A method of treating peripheral vascular diseases, which comprises topically or systemically administering to a mammalian host an effective amount of a compound as defined in claim 1 or a pharmaceutically acceptable salt thereof.

* * * * *

UNITED STATES PATENT AND TRADEMARK OFFICE

CERTIFICATE OF CORRECTION

PATENT NO. : 4,734,424

DATED : March 29, 1988

INVENTOR(S) : Steven E. Hall et al.

It is certified that error appears in the above-identified patent and that said Letters Patent is hereby corrected as shown below:

Column 63, line 20 should read --or a single bond; R is $CO_2H$, $CO_2$alkyl, $CO_2$ alkali metal,--.
Column 63, line 34, "$r^3$" should read --$R^3$--.
Column 63, line 37, "lower alkyl-s-" should read --lower alkyl-S- --.
Column 64, line 25, after "CH=CH", insert --or--.
Column 64, line 40, after "[2.2.1" insert --]--.
Column 64, line 39, after the "]" insert - --.

Signed and Sealed this

Thirtieth Day of August, 1988

*Attest:*

DONALD J. QUIGG

*Attesting Officer*

*Commissioner of Patents and Trademarks*